US007642068B2

(12) United States Patent
Steiner et al.

(10) Patent No.: US 7,642,068 B2
(45) Date of Patent: Jan. 5, 2010

(54) MULTIPLE-VALENT OPSONOPHAGOCYTIC ASSAY SELECTION PANEL ARRAYS AND USES THEREFOR

(75) Inventors: Sandra Steiner, Atlanta, GA (US); Patricia F. Holder, Mableton, GA (US); George M. Carlone, Stone Mountain, GA (US); GowriSankar Rajam, Tucker, GA (US)

(73) Assignee: The United States of America as represented by the Department of Health and Human Services, Center for Disease Control and Prevention, Washington, DC (US)

(*) Notice: Subject to any disclaimer, the term of this patent is extended or adjusted under 35 U.S.C. 154(b) by 0 days.

(21) Appl. No.: 11/910,517

(22) PCT Filed: Apr. 21, 2006

(86) PCT No.: PCT/US2006/015499

§ 371 (c)(1),
(2), (4) Date: Oct. 2, 2007

(87) PCT Pub. No.: WO2006/116325

PCT Pub. Date: Nov. 2, 2006

(65) Prior Publication Data

US 2008/0193966 A1 Aug. 14, 2008

Related U.S. Application Data

(60) Provisional application No. 60/674,197, filed on Apr. 22, 2005.

(51) Int. Cl.
*C12Q 1/18* (2006.01)
*C12Q 1/00* (2006.01)
*G01N 33/43* (2006.01)
*G01N 33/567* (2006.01)
*C12Q 1/20* (2006.01)

(52) U.S. Cl. .............................. 435/32; 435/4; 435/7.1; 435/7.2; 435/7.34

(58) Field of Classification Search .................. None
See application file for complete search history.

(56) References Cited

U.S. PATENT DOCUMENTS

| 5,501,959 A | 3/1996 | Lancaster et al. |
| 6,437,108 B1 | 8/2002 | Youngman et al. |
| 6,815,172 B1 | 11/2004 | Martinez et al. |

FOREIGN PATENT DOCUMENTS

WO WO 00/77518 A3 12/2000

OTHER PUBLICATIONS

Bogaert et al. Vaccine 22 (2004) 4014-4020 (available online Apr. 23, 2004).*

Franzblau et al. Journal of Clinical Microbiology, Feb. 1998, p. 363-366.*
Coffey et al. Microbiology (1999), 145, 2023-2031.*
Bieging et al., "A Rapid Fluorescent Multivalent Opsonophagocytic Assay (fmOPA) for Determination of Functional Anti-Polysaccharide Antibodies to *Streptococcus pneumoniae*," in program and abstracts of the 105th General Meeting of the American Society for Microbiology 2005, Poster V-001, p. 217, American Society for Microbiology, Atlanta, GA.
Bieging et al., "Fluorescent Multivalent Opsonophagocytic Assay for Measurement of Functional Antibodies to *Streptococcus pneumoniae*," *Clin. Diagn. Lab. Immunol.* 12:1238-1242, 2005.
Bogaert et al., "Multiplex Opsonophagocytosis Assay (MOPA): A Useful Tool for the Monitoring of the 7-Valent Pneumococcal Conjugate Vaccine," *Vaccine* 22:4014-4020, 2004.
Kim et al., "Efficiency of a Pneumococcal Opsonophagocytic Killing Assay Improved by Multiplexing and by Coloring Colonies," *Clin. Diagn. Lab. Immunol.* 10:616-621, 2003.
Lin et al., "Chromogenic Assay Measuring Opsonophagocytic Killing Capacities of Antipneumococcal Antisera," *Clin. Diagn. Lab. Immunol.* 8:528-533, 2001.
McBride et al., "Development of Colorimetric Microtiter Plate Assay for Assessment of Antimicrobials against *Acanthamoeba*," *J. Clin. Micriobiol.* 43:629-634, 2005.
Millen et al., "Antibody-Mediated Neutralization of Pertussis Toxin-Induced Mitogenicity of Human Peripheral Blood Mononuclear Cells," *Infect. Immun.* 72:615-620, 2004.
Mountzouros and Howell, "Detection of Complement-Mediated Antibody-Dependent Bactericidal Activity in a Fluorescence-Based Serum Bactericidal Assay for Group B *Neisseria meningitidis*," *J. Clin. Micriobiol.* 38:2878-2884, 2000.
Nahm et al., "Development of a Multi-Specificity Opsonophagocytic Killing Assay," *Vaccine* 18:2768-2771, 2000.
Rodríguez et al., "Standardization of *Neisseria meningitidis* Serogroup B Colorimetric Serum Bactericidal Assay," *Clin. Diagn. Lab. Immun.* 9:109-114, 2002.
Romero-Steiner et al., "Standarization of an Opsonophagocytic Assay for the Measurement of Functional Antibody Activity against *Streptococcus pneumoniae* Using Differentiated HL-60 Cells," *Clin. Diagn. Lab. Immun.* 4:415-422, 1997.
Romero-Steiner et al., "Multilaboratory Evaluation of a Viability Assay for Measurement of Opsonophagocytic Antibodies Specific to the Capsular Polysaccharides of *Streptococcus pneumoniae*," *Clin. Diagn. Lab. Immun.* 10:1019-1024, 2003.
Romero-Steiner et al., "Measurement of Serum Bactericidal Activity Specific for *Haemophilus influenzae* Type b by Using a Chromogenic and Fluorescent Metabolic Indicator," *Clin. Diag. Lab. Immun.* 11:89-93, 2004.

(Continued)

*Primary Examiner*—David J. Blanchard
*Assistant Examiner*—Oluwatosin Ogunbiyi
(74) *Attorney, Agent, or Firm*—Klarquist Sparkman, LLP

(57) ABSTRACT

This application discloses a multivalent opsonophagocytosis assay that does not rely on counting of bacterial colonies to determine bacteria viability following opsonophagocytosis. Instead, the method uses a metabolic colorimetric indicator to determine if viable bacteria are present. Also disclosed are arrays that can be used to determine the viability of bacteria following opsonophagocytosis.

18 Claims, 6 Drawing Sheets

OTHER PUBLICATIONS

Morbidity and Mortality Weekly Report, Department of Health and Human Services, Centers for Disease Control and Prevention, vol. 53, pp. 1007-1034, 2004.

Glass et al., "Detection of Serum Bactericidal Activity to *Neisseria meningitidis* Groups A, C, Y, and W135 Using a Fluorescent Metabolic Indicator," In Program and abstracts of the International Conference on Emerging Infectious Diseases 2004, Atlanta, Georgia.

Hu et al., "Approach to Validating an Opsonophagocytic Assay for *Streptococcus pneumonia*," *Clin. Diagn. Lab. Immunol. 12*:287-295, 2005.

* cited by examiner

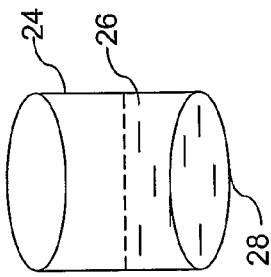
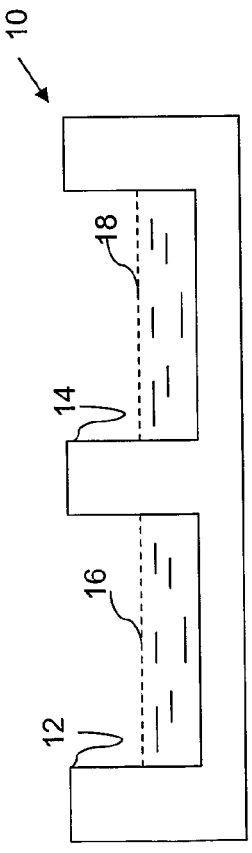
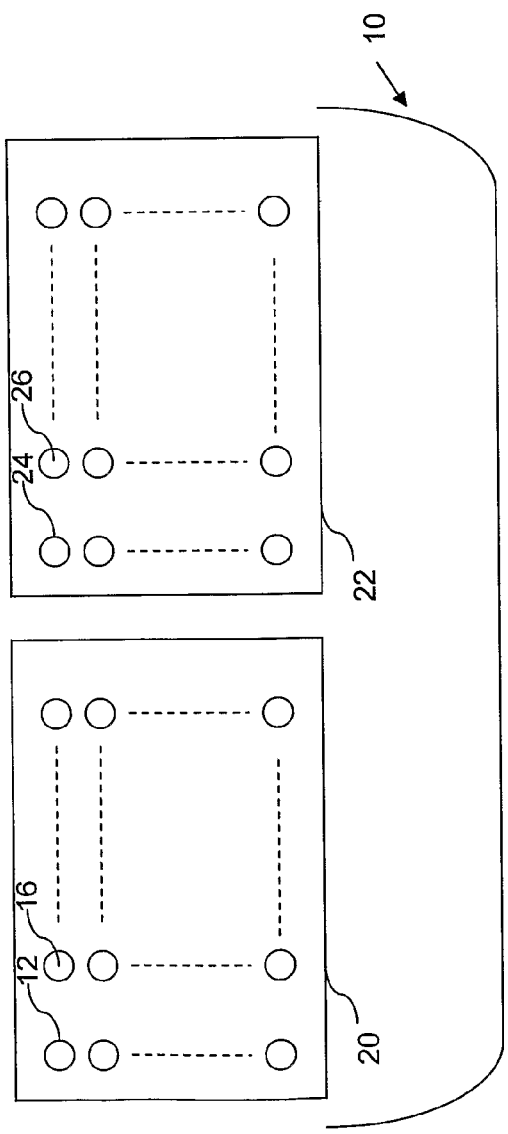

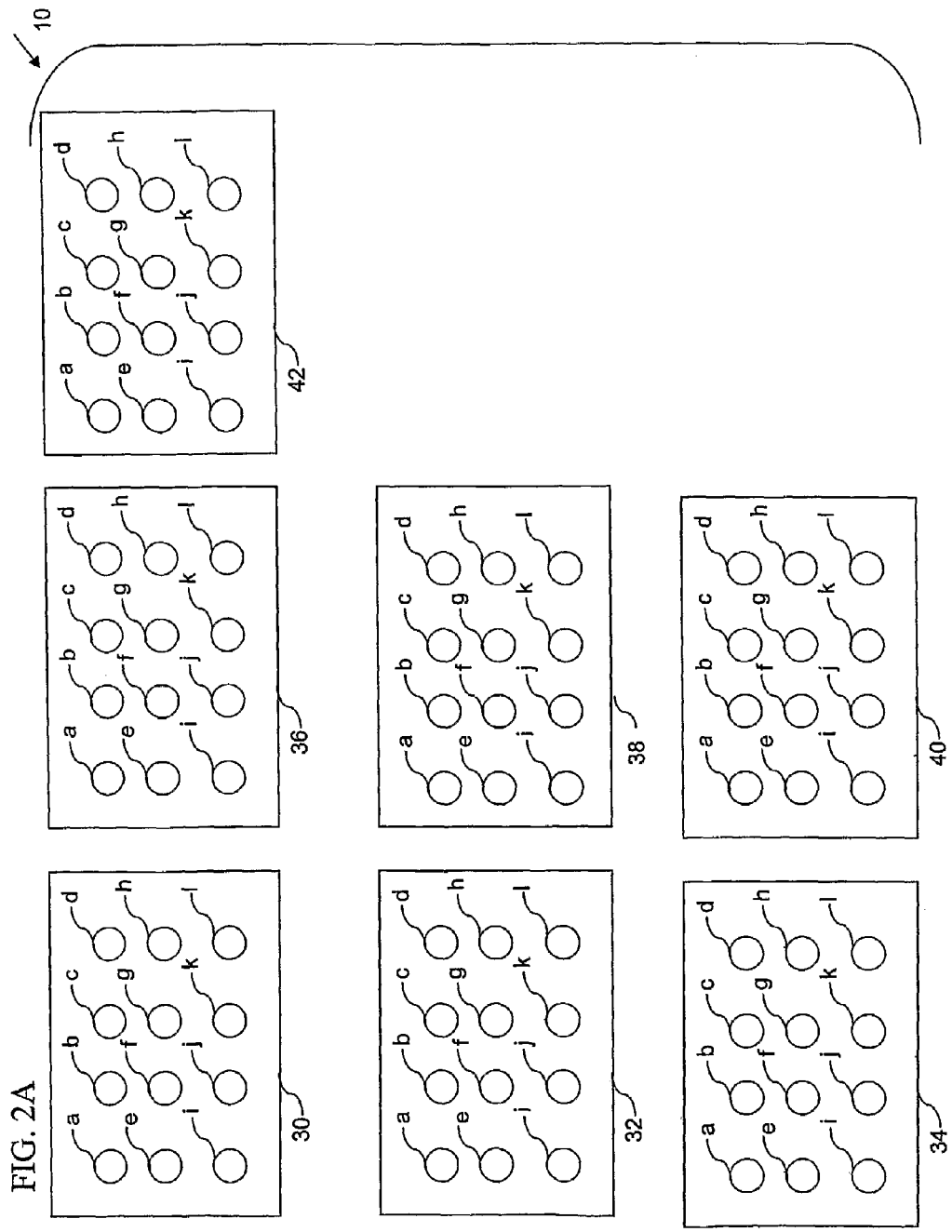

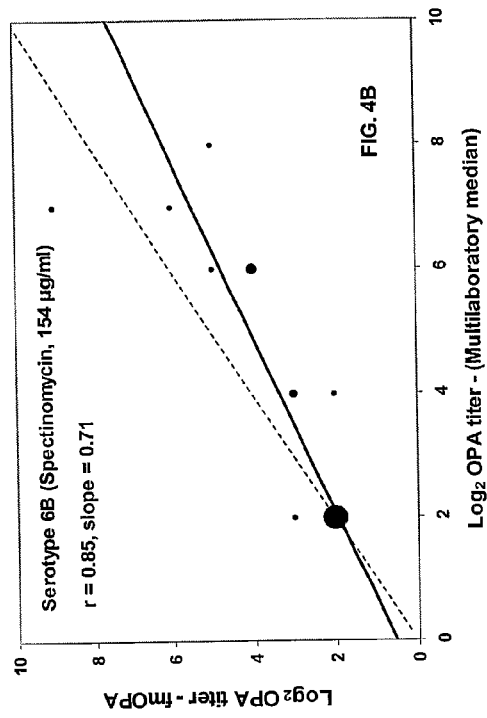
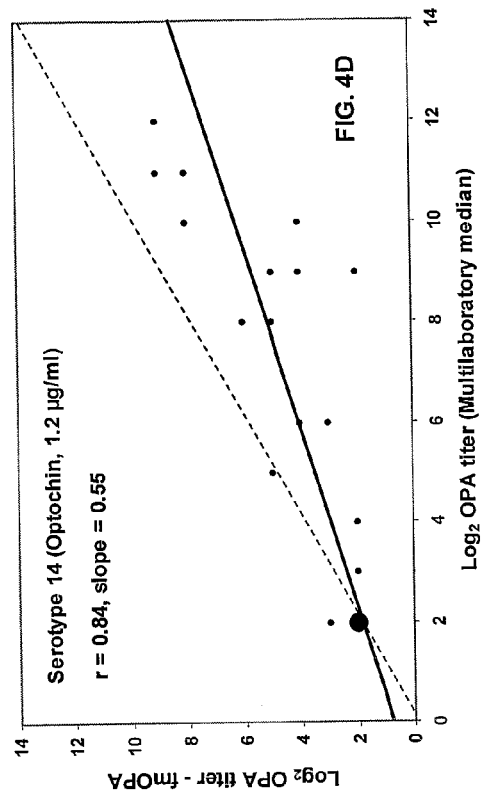
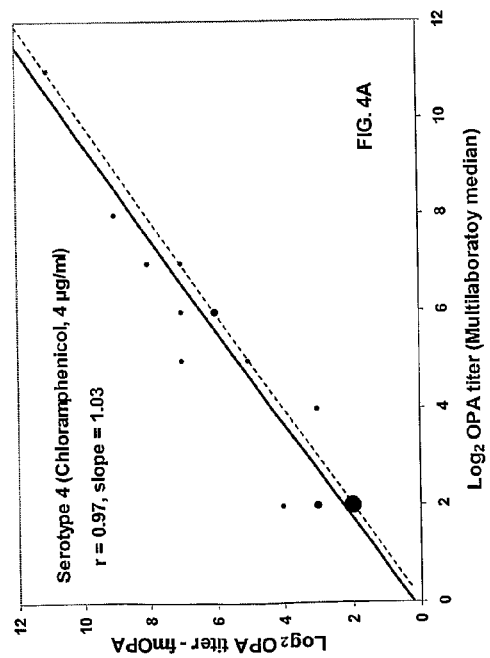
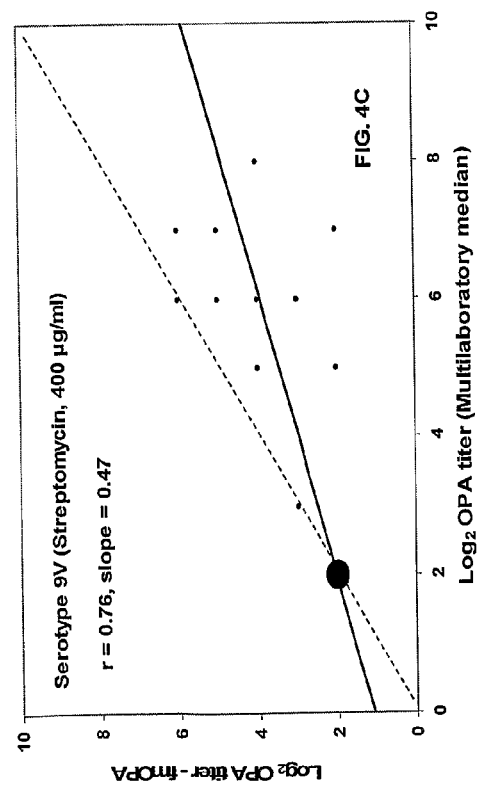
FIG. 4A
FIG. 4B
FIG. 4C
FIG. 4D

MULTIPLE-VALENT OPSONOPHAGOCYTIC ASSAY SELECTION PANEL ARRAYS AND USES THEREFOR

CROSS-REFERENCE TO RELATED APPLICATIONS

This is the U.S. National Stage of International Application No. PCT/US2006/015499, filed Apr. 21, 2006 (published in English under PCT Article 21(2)), which claims the benefit of U.S. Patent Application No. 60/674,197 filed Apr. 22, 2005, herein incorporated by reference in entirety.

FIELD

The present application relates to methods of detecting viable or non-viable serotype-specific antibiotic-resistant bacteria as an indicator of the presence or absence of functional antibodies, and arrays that can be used for such detection.

BACKGROUND

Within the last decade, the emergence of multi-drug resistant pathogens has led to the increased use of vaccines as a method of treating infectious disease. New vaccines are being developed at a rapid pace, and assays to determine the in vivo effectiveness of these vaccines are also being developed. Several assays have been developed that determine the effectiveness of vaccines by detecting vaccine-specific antibodies generated in vivo after vaccine administration. These assays include radioantigen binding assays and enzyme-linked immunosorbant assays (ELISAs) (Schiffman et al., *J. Immunol. Meth.* 33:133-44, 1980; Nahm et al., *J. Infect. Dis.* 173: 113-8, 1996; Quataert et al., *Clin. Diagn. Lab. Immunol.* 2:590-7, 1995). One problem with these assays is that they measure the total amount of antibody generated in response to administration of the vaccine, without regard to whether the antibodies actually provide a protective response in the immunized individual. Therefore, total antibody assays do not provide an accurate estimation as to the in vivo effectiveness of a vaccine.

Whether a vaccine provides protective immunity or simply generates an antibody response depends upon the type of infection the vaccine seeks to prevent as well as the type of antibodies generated in response to administration of the vaccine. For example, a protective immune response to pathogens such as *Streptococcus pneumoniae* involves opsonophagocytosis of the infectious agents. Opsonophagocytosis is the binding (or opsonization) of antibodies and complement (or complement components) to the infectious agent, and the subsequent uptake of the infectious agent by effector cells via the binding of the effector cells to the antibody/antigen complex. Therefore, a protective immune response against such pathogens includes more than the mere generation of antibodies that bind the pathogen. A protective immune response includes the generation of "functional" antibodies that bind to the infectious agents and also provide a means for uptake and clearance by effector cells. Another aspect of functionality is the ability to interact with complement reactions that may be involved in opsonophagocytosis.

One functional assay that has been developed to measure the effectiveness of vaccines is the opsonophagocytic assay. Opsonophagocytic assays more closely resemble animal models, and appear to provide a closer correlation with serotype-specific vaccine effectiveness than other prior art assays such as ELISAs (Wenger et al., Laboratory correlates for protective effectiveness of pneumococcal vaccines: how can they be identified and validated? Abstr. G37 in Program and abstracts of the 36th Interscience Conference on Antimicrobial Agents and Chemotherapy, 1996). Measurement of the effectiveness of a vaccine designed to provide protection against infection by multiple serotypes of a pathogen involves measurement of multiple functional antibodies generated toward each different serotype. Although the functional assays described above can be run multiple times for each different serotype present in the vaccine, such a practice can be time consuming, labor intensive, and require a large quantity of serum for evaluation. These difficulties can be partially alleviated by evaluating multiple serotypes simultaneously (for example see Bogaert et al., *Vaccine,* 22:4014-20, 2004; Kim and Nahm, *Clin. Diag. Lab. Immunol.* 10:616-21, 2003; and Martinez et al., *Clin. Diag. Lab. Immunol.* 6:581-586, 1999). However, the method of Martinez et al. (*Clin. Diag. Lab. Immunol.* 6:581-586, 1999) can be limited by the number of fluorophores that can be simultaneously detected by the flow cytometer, and the methods of Bogaert et al. (*Vaccine,* 22:4014-20, 2004) and Kim and Nahm (*Clin. Diag. Lab. Immunol.* 10:616-21, 2003) involve waiting for growth of bacterial colonies, and then counting the colonies, which can be time consuming.

Therefore, a rapid, automated, assay is needed, particularly one that can simultaneously measure functional antibodies directed against multiple serotypes of pathogens in a single day.

SUMMARY

The inventors have demonstrated that a metabolic indicator such as Alamar Blue™ can be used in a multivalent opsonophagocytic assay (mOPA) to determine if functional anti-polysaccharide antibodies to *Streptococcus pneumoniae* are present in a sample obtained from a subject vaccinated with a multivalent vaccine or after exposure to a bacterial pathogen. Multiple serotypes can be evaluated in a single multivalent assay, which significantly reduces the time and amount of sera needed to determine if functional antibodies are present. For example, the metabolic indicator provides a fluorometric indicator of bacterial growth. As a result, growth of bacteria into colonies is not needed, nor is there a need for colony counting. In particular examples, the disclosed assay are suitable for same-day mOPA titer determinations.

Methods are disclosed for performing a functional assay for determining whether antibodies that promote complement-mediated opsonophagocytic activity are present in a sample, such as a plurality of different functional antibodies against multiple bacterial serotypes. Such methods can be used to test multivalent vaccines, such as those for gram-positive bacteria, for example *Streptococcus pneumoniae*.

In particular examples, the method includes incubating effector cells, complement, a plurality of different serotype-specific antibiotic-resistant bacteria, and a test biological sample in the presence of a medium that supports viability of the effector cells. Both the complement and effector cells are present in a sufficient amount to kill the serotype-specific antibiotic-resistant bacteria in the presence of functional antibodies that specifically recognize the bacteria. Following opsonophagocytosis, bacteria are introduced into a liquid growth medium, containing a growth inhibitory substance and a metabolic indicator, for example a colorimetric indicator, that indicates bacterial viability, such as a medium that supports the growth of at least one of the plurality of different serotype-specific antibiotic-resistant bacteria, but does not support the growth of other members of the plurality of different serotype-specific antibiotic-resistant bacteria. For example, the first growth medium can support the growth of a first of the plurality of different serotype-specific antibiotic-resistant bacteria, by containing a first growth inhibitory substance to which the first of the plurality of different serotype-specific antibiotic-resistant bacteria is resistant such that the first bacteria grows in the first growth medium. Subsequently, the metabolic indicator is detected, for example by detecting a colorimetric change in the medium (such as an increase or decrease of a particular wavelength of light, for example relative to a positive or negative control). Such a change in color indicates bacterial viability (such as the metabolic activity of viable bacteria or the cell permeability of non-viable bacteria), wherein an absence of viability is an indicator that the test serum contains functional antibodies that promote complement-mediated opsonophagocytic activity against the first of the plurality of different serotype-specific antibiotic-resistant bacteria. In particular examples, the method does not include counting bacterial colonies to detect bacterial viability. A diffuse color present in the medium can serve as an indicator of viability or non-viability.

In particular examples, following opsonophagocytosis, surviving serotype-specific antibiotic-resistant bacteria are introduced into several different liquid growth media, wherein each growth medium supports the growth of a target serotype-specific antibiotic-resistant bacteria, but does not support the growth of the other serotype-specific antibiotic-resistant bacteria present. In some examples, bacteria are introduced into at least seven different liquid growth media, wherein each growth medium includes a growth inhibitory substance, such as an antibiotic, to which the target serotype-specific antibiotic-resistant bacteria is resistant, but to which the other serotype-specific antibiotic-resistant bacteria are not resistant (and are therefore killed by the growth inhibitory substance). By determining whether multiple serotype-specific antibiotic-resistant bacteria survive opsonophagocytosis by introducing the bacteria into several different liquid growth media (each containing a particular or different growth inhibitory substance), whether a biological sample from a mammalian subject (such as a human or veterinary subject) contains one or more of a plurality of different functional antibodies against multiple bacterial serotypes can be determined.

In one example, the method detects a plurality of serotype-specific antibiotic-resistant bacteria following opsonophagocytosis as an indictor of the presence of a plurality of different functional antibodies against multiple bacterial serotypes. For example, the method can include combining a biological sample (such as a serum sample) with a plurality of different serotype-specific antibiotic-resistant bacteria, complement, and effector cells, thereby generating a first reaction mixture. The first reaction mixture is incubated for a period of time sufficient to permit opsonophagocytosis of the bacteria by the effector cells, thereby generating a second reaction mixture. The second reaction mixture, or a portion thereof (such as one containing bacteria, or one sufficiently free of effector cells), is incubated with a plurality of different growth media. Each growth medium can include a different growth inhibitory substance, and a metabolic indicator that indicates bacterial viability, wherein the plurality of different serotype-specific antibiotic-resistant bacteria are resistant to and can grow in at least one of the different growth inhibitory substances, but not in the other growth inhibitory substances. A signal from the metabolic indicator is detected, wherein a change in signal as compared to a control sample indicates opsonophagocytic killing of the bacteria and the presence of functional antibodies in the sample against multiple bacterial serotypes. For example, an increase in signal (such as compared to a negative control, for example, one containing only bacteria that are not resistant to the growth inhibitory substance), indicates that the serotype-specific antibiotic-resistant bacteria that are resistant to that growth inhibitory substance survived, and therefore the sample does not contain functional antibodies against that bacterial serotype. In contrast, a decrease in signal (such as compared to a positive control, for example, one containing bacteria that are resistant to the growth inhibitory substance), indicates that the serotype-specific antibiotic-resistant bacteria that are resistant to that growth inhibitory substance were killed, and therefore the sample contains functional antibodies against that bacterial serotype.

Also provided by the present disclosure are arrays for detecting a plurality of different functional antibodies against multiple bacterial serotypes. In some examples, the array includes a plurality of containers, wherein each container contains a growth inhibitory substance (such as an antibiotic) associated with a target bacteria for that container, a growth medium that supports growth of the target bacteria associated with that container, and a metabolic indicator that indicates bacterial viability. The target bacteria associated with each container are resistant to and grow in the growth inhibitory substance associated with that container, but are not resistant to and do not grow in the presence of other growth inhibitory substances associated with other containers of the array. In some examples, the target bacteria include serotype-specific antibiotic-resistant bacteria. In particular examples, the growth medium is a liquid medium, and does not include agar, gelatin, or other hardening substance. However, the liquid in the containers can be frozen for later use.

In particular examples, the containers are wells present on at least one detection plate or panel, such as at least seven panels, wherein each panel includes a different growth inhibitory substance associated with a target serotype-specific antibiotic-resistant bacteria for that panel, wherein the target bacteria associated with each panel are resistant to and grow in the growth inhibitory substance associated with that panel, but are not resistant to and do not grow in the presence of other growth inhibitory substances associated with the other panels. In some examples, the plates or panels are not opaque, but are transparent. In some example, the plate is a multi-well plate, such as a 96-, 384- or 1536-well plate, which are known in the art.

The foregoing and other objects, features, and advantages of the invention will become more apparent from the following detailed description, which proceeds with reference to the accompanying figures.

BRIEF DESCRIPTION OF THE DRAWINGS

FIG. 1A is a schematic drawing of an exemplary array 10.

FIG. 1B is a schematic drawing of an exemplary array 10 that includes multiple detection plates or panels 20 and 22, each containing a plurality of containers 12, 24.

FIG. 1C is a schematic drawing of an exemplary container 24 that includes a bottom 28, and can include growth medium 26.

FIG. 2A is a schematic drawing showing an exemplary multi-well multi-plate embodiment.

FIGS. 4A-4G are graphs comparing fluorescent multivalent OPA (fmOPA) titers to the median OPA titers from a multilabortory study (Romero-Steiner et al., *Clin. Diag. Lab. Immunol.* 10:1019-24, 2003). The solid line is the linear regression; the dotted line is the line of identity. The area of the data point represents the number of sera that at that coordinate. (A) serotype 4, (B) serotype 6B, (C) serotype 9V, (D) serotype 14, (E) serotype 18C, (F) serotype 19F, and (G) serotype 23F.

DETAILED DESCRIPTION

Abbreviations and Terms

Figure 2B:
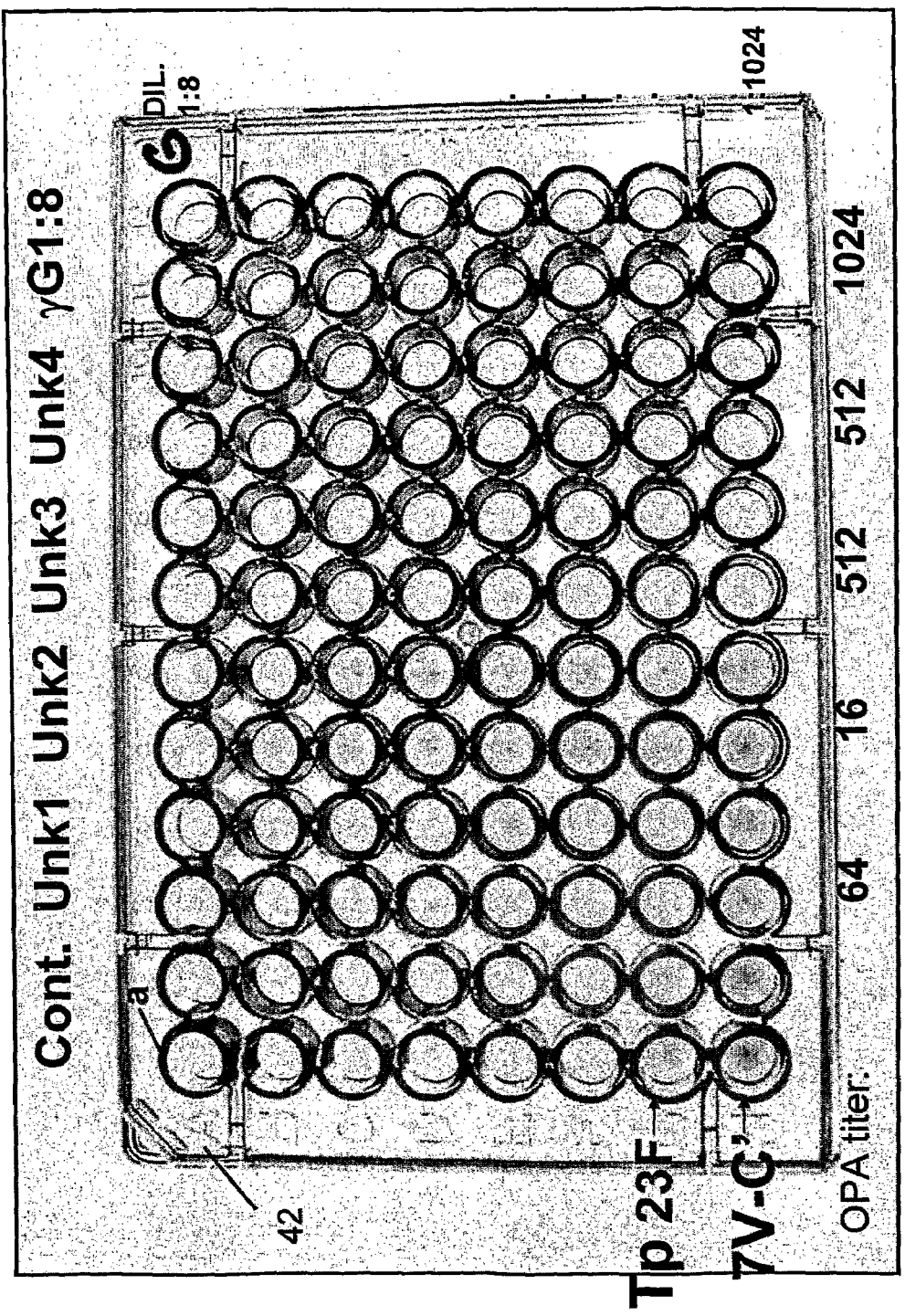
FIG. 2B is a digital image showing an exemplary 96-well multi-well multi-plate embodiment. This image shows the results of one of seven detection panels. This particular panel corresponds to serotype 23F.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a container" includes single or plural containers and is considered equivalent to the phrase "comprising at least one container" or to the phase "comprising one or more containers." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Antigen: A compound, composition, or substance that can stimulate the production of antibodies (such as functional antibodies) or a T-cell response in a mammal, including compositions that are injected, absorbed or otherwise introduced into a mammal. Examples include, but are not limited to, peptides, lipids, polysaccharides, and nucleic acids containing antigenic determinants, such as those recognized by an immune cell. In one example, antigens include peptides derived from different serotypes or strains of a pathogen, such as different serotypes of a gram positive bacterium (for example *Streptococcus pneumoniae*). In another example, antigens include peptides derived from multiple pathogens. Exemplary pathogens include bacteria, fungi and parasites.

Antibody: Immunoglobulins and immunologically active portions ("fragments") thereof, such as molecules that include an antigen binding site that specifically binds (immunoreacts with) an antigen. A naturally occurring antibody (such as IgG, IgM, and IgA) includes four polypeptide chains, two heavy (H) chains and two light (L) chains interconnected by disulfide bonds. Examples of immunologically active portions thereof, include, but are not limited to, Fab, Fab', F(ab')$_2$, Fabc and Fv portions. Functional antibodies are antibodies that specifically bind to an antigen, can efficiently allow for complement fixation, and also interact with an effector cell, wherein the interaction of the antibody and effector cell results in internalization of the antibody by the effector cell.

Antibiotic: An agent, such as a chemical substance produced by a microorganism, or synthetically generated, which can kill or inhibit the growth of a microorganism, such as a bacterium. Particular examples include, but are not limited to, chloramphenicol, spectinomycin, streptomycin, erythromycin, rifampicin, tetracycline, trimethoprim, penicillin, tetracycline, optochin, vancomycin, levomycin, or combinations thereof.

Array: An arrangement of containers in addressable locations on or in a substrate. In one example, an array includes a multi-container (or multi-well) plate, wherein the containers include growth medium and a metabolic indicator. In yet another example, an array includes a plurality of multi-well plates, which in some examples is referred to as a panel array.

The array of containers ("features") makes it possible to carry out a very large number of analyses at one time. The number of addressable locations on the array can vary, for example from at least 4, to at least 6, at least 8, at least 12, at least 16, at least 24, at least 48, at least 96, at least 150, at least 384, at least 672, at least 1536, or more. Within an array, each container is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each container is assigned, and a key can be provided to correlate each location with the appropriate target or feature position. Often, ordered arrays are arranged in a symmetrical grid pattern, but containers can be arranged in other patterns (such as in radially distributed lines, spiral lines, or ordered clusters). Addressable arrays usually are computer readable, in that a computer can be programmed to correlate a particular address on the array with information about the containers at that position (such as viability data, including for instance signal intensity). In some examples of computer readable formats, the individual features in the array are arranged regularly, for instance in a Cartesian grid pattern, which can be correlated to address information by a computer.

Colorimetric: A type of chemical analysis in which a color change is associated with a chemical change. Although colorimetric can include assays in which a quantitative analysis is associated with a measurement of a color change, the term is not used herein to imply or require a quantitative analysis. Hence, qualitative changes, such as a visible change in color, can be associated with a change being measured (such as the viability or non-viability of a cell, such as a bacterium, in a sample, or the presence or absence of metabolic processes associated with viable cells). A color change broadly includes any detectable change, for example a change in wavelength, intensity, fluorescence, and so forth.

Complement: A plasma protein system involved in immune defense. Following activation by antigen-antibody complexes, complement proteins lyse antigenic cells, attract phagocytic cells, and assist in the destruction of antigenic cells by phagocytosis. In particular examples, complement is provided in the form of serum, such as baby rabbit serum. In some examples, complement is freeze-dried prior to use.

Container: The terms container, well, or receptacle are general terms that refer to any appropriate structure for holding things, such as liquids, for example, growth media that contains a growth inhibitory substance and a metabolic indicator. In a particular example, the bottom of the container is transparent.

Effector cells: Cells capable of binding to antibody/antigen complexes and internalizing such complexes. In particular examples, effector cells express Fc receptors, such as FcγRI, FcγRII and FcγRIII that bind to antibody/antigen complexes and facilitate internalization. In some examples, effector cells are derived from the serum of an individual (such as peripheral blood leukocytes, PBLs) or from an in vitro culture. Examples of effector cells include, but are not limited to: macrophages, mononuclear phagocytes, natural killer cells, and granulocytes such as neutrophils and eosinophils. In a particular example, the effector cell is a differentiated human promyelocytic leukemia cell, such as differentiated HL-60 cells.

Gram positive bacteria: Bacteria having a cell wall with no outer membrane, which resist decolorization with alcohol after being treated with Gram crystal violet stain, imparting a violet color to the bacterium when viewed by light microscopy. In particular examples, the outer structure of the gram positive bacterium includes a cytoplasmic membrane surrounded by a thick, rigid bacterial cell wall composed of peptidoglycan. Examples include, but are not limited to, *Streptococcus, Staphylococcus, Listeria, Clostridium, Propionibacterium*, as well as the bacterium responsible for diphtheria (*Cornynebacterium diphtheriae*) and anthrax (*Bacillus anthracis*). The methods and arrays disclosed herein can be used to determine if a sample includes functional antibodies to any target serotype of a target gram-positive bacterium.

Growth inhibitory substance: An agent, alone or in combination with other agents, that prevents the growth of a cell (such as a bacterial cell) that is not resistant to the growth inhibitory substance. However, agents that are resistant to the growth inhibitory substance can grow in the growth inhibitory substance. Examples include, but are not limited to, antibiotics, detergents, chemotherapeutic agents, and metabolic inhibitors.

Growth medium: A substance or preparation used for the cultivation of living cells, including microorganisms such as bacteria. In particular examples, such medium includes nutrients for the target cells. A liquid growth medium is one that does not contain agar in sufficient amounts to cause hardening or solidification of the medium. In a particular example, a liquid growth medium does not contain agar or other gelling or hardening agents.

Immunize: To administer one or more antigens to a subject, which desirably produces an immune response, such as the production of functional antibodies. In a particular example, a mammal is immunized by administering to the mammal a vaccine that includes one or more serotypes of a gram-positive bacterium.

Metabolic indicator: An agent that can be used to detect metabolic activity of a cell, for example to determine whether a cell is viable or proliferating, such as determining whether a bacterium is viable. In particular examples, metabolic indicators provide a colorimetric reaction, wherein the presence or absence of a particular color (such as fluorescence) indicates whether the cells are viable or not.

Examples include, but are not limited to, Alamar Blue™ (resazurin) (viable cells emit fluorescence which can be detected at 590 nm; dead cells produce no detectable fluorescence at 590 nm; dodecyl resazurin ($C_{12}$-resazurin) (Molecular Probes, Eugene Oreg.); fluorescein diacetate (FDA) (viable cells convert FDA to the fluorescent compound fluorescein which can be detected; dead cells produce no detectable fluorescein); and fluorogenic redox indicator 5-cyano-2,3-ditolyltetrazolium chloride (CTC) (viable cells emit red fluorescence which can be detected at 590 nm; dead cells produce no detectable fluorescence at 590 nm).

Other particular examples include cell-impermeant nucleic acid stains to detect the dead-cell population. Examples include but are not limited to, SYTOX Green nucleic acid stain (Molecular Probes, Eugene, Oreg.) (504 excitation/523 emission dead bacteria fluoresce bright green when excited at 488 nm) and SYTOX Blue nucleic acid stain (445 excitation/ 470 emission Molecular Probes, Eugene, Oreg.) (dead bacteria fluoresce blue when excited at 436 nm).

Minimum inhibitory concentration (MIC): The lowest concentration of an antibiotic that inhibits growth of an organism, such as a bacterium.

Multivalent opsonophagocytic assay: A method of simultaneously (or nearly simultaneously) measuring the opsonophagocytosis against multiple serotypes, such as two or more serotypes present in a vaccine. Such an assay can be use to determine the effectiveness of a multivalent vaccine in a mammalian subject, such as a human, by determining whether one or more functional antibodies that are specific for the serotypes presence in the vaccine are present in the subject.

Opsonophagocytosis: The phagocytosis by effector cells (such as macrophages and monocytes) in the presence of specific serum opsonins. Opsonins include any substance that binds to particulate antigens and induces their phagocytosis by effector cells. Exemplary opsonins include opsonizing antibodies (IgM, IgG1, IgG2, IgG3 and IgA immunoglobulins specific for the antigen) and certain complement fragments (C3b, iC3b, C3d, and C4b, which become bound to the antigen during complement activation), both of which trigger phagocytosis by binding to specific cell-surface receptors (such as Fc receptors and C3b receptors on neutrophils and macrophages, and C3d receptors on macrophages).

Sample: A biological specimen, such as one that contains nucleic acid molecules (such as cDNA or mRNA), proteins, functional antibodies, pathogens, or combinations thereof. In a particular example, a sample includes functional antibodies developed in response to a vaccine, such as a multivalent vaccine. Exemplary samples include, but are not limited to: peripheral blood, plasma, serum, urine, saliva, tissue biopsy, surgical specimen, amniocentesis samples, cerebrospinal fluid, ear fluid, bronchial washes, and autopsy material. A test sample is a sample to be analyzed, for example to be analyzed for the presence of functional antibodies using the methods or arrays disclosed herein.

Serotype: The genotype of a unicellular organism, such as a bacterium, as defined by antisera against antigenic determinants expressed on the surface. Also refers to the antigens themselves.

Specifically bind: When referring to an opsonin (such as an antibody), refers to a binding reaction which is determinative of the presence of a target protein, peptide, or polysaccharide in the presence of a heterogeneous population of proteins and other biologics. Thus, under designated conditions, an antibody binds preferentially to a particular target protein, peptide or polysaccharide (such as a bacterial capsular polysaccharide) and do not bind in a significant amount to other proteins or polysaccharides present in the sample.

Subject: Living multi-cellular vertebrate organisms, including human and veterinary subjects. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Transparent: A substance is transparent if light can be transmitted though it, for example it can be seen through. Ideally, a detection plate is composed of a transparent substance.

Vaccine: A pharmaceutical composition that elicits a prophylactic or therapeutic immune response in a subject. In some cases, the immune response is a protective immune response. Typically, a vaccine elicits an antigen-specific immune response to at least one antigen of a pathogen. In one example, a vaccine elicits an immune response against a gram-positive bacterium, such as *Streptococcus pneumoniae*.

Arrays for Multivalent Opsonophagocytic Assays

Provided herein are arrays that can be used to determine the results of a multivalent opsonophagocytic assay, for example by detecting serotype-specific antibiotic-resistant bacteria as an indicator of the presence of functional antibodies against the serotypes. Such arrays therefore can be used to determine if a sample from a subject contains different functional antibodies against multiple bacterial serotypes, for example to determine the effectiveness of a multivalent vaccine administered to a subject, or to determine if the subject has been exposed to a particular pathogen.

Exemplary arrays of the present disclosure are shown in FIGS. 1A and 1B. As shown in FIG. 1A, in one example the array 10 includes a plurality of containers 12, 14. In particular examples, the shape of the container is a flat-bottomed container. However, one skilled in the art will appreciate that other shapes can be used, such as a round-bottomed container. The containers 12, 14 contain a growth medium 16 and 18 that supports growth of the target bacteria associated with that container. Each growth medium includes a different growth inhibitory substance associated with a target bacterium for that container as well as a metabolic indicator that indicates bacterial viability. The target bacteria associated with each container are resistant to and grow in the growth inhibitory substance associated with that container, but are not resistant to and do not grow in the presence of other growth inhibitory substances associated with other containers of the array. For example, container 12 can contain the antibiotic chloramphenicol for selecting bacteria that are resistant to chloramphenicol, and a container 14 can contain the antibiotic spectinomycin for selecting bacteria that are resistant to spectinomycin.

Although only two containers are shown in FIG. 1A, and the array is not limited to containing a particular number of containers. For example, in FIG. 1B, a plurality of plates 20, 22 are provided having a plurality of containers 12, 24. A more detailed view of an exemplary container 24 is shown in FIG. 1C, wherein container 24 includes growth medium 26, and a bottom 28. In some examples, the detection plates 20, 22 (or a portion thereof, such as the bottom 28) are made of a transparent material, for example not a white or opaque plastic. Suitable materials for the detection plate 20, 22 include, but are not limited to: polypropylene, polystyrene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference).

In particular examples, the detection plates 20, 22 include at least 96 containers 12, 24. For example, if the detection plate 20, 22 is a 96 well-detection plate, the containers 12, 24 can be in a spaced apart alignment to define a matrix of eight rows and twelve columns. The target bacteria associated with each plate 20, 22 are resistant to and grow in the growth inhibitory substance associated with that plate, but are not resistant to and do not grow in the presence of other growth inhibitory substances associated with the other plates. For example, as shown in FIG. 1B, bacteria associated plate 20 are resistant to and grow in the growth medium 16 containing the growth inhibitory substance associated with that plate 20, but are not resistant to and do not grow in the growth medium 26 containing the growth inhibitory substance associated with other plate 22.

In particular examples, the growth medium 16, 18, 26 is a liquid medium. For example, the growth medium 16, 18, 26 can include a broth suitable for growing the bacteria of interest. In a particular example, the growth medium 16, 18, 26 does not contain agar, or does not contain sufficient amounts of agar or other hardening agent (such as gelatin) to cause solidification of the growth medium 16, 18, 26. However, in some examples the growth medium 16, 18, 26 is frozen, for example when the array 10 is frozen for storage and use at a later date.

The growth inhibitory substance in the growth medium 16, 18, 26 can include any agent that prevents the growth, and in some examples kills otherwise viable cells, such as bacterial cells. In a particular example, the growth inhibitory substance is present at ½ of the minimum inhibitory concentration (MIC). In one example, the growth inhibitory substance includes an antibiotic, such as chloramphenicol, spectinomycin, streptomycin, erythromycin, rifampicin, tetracycline, trimethoprim, optochin, or penicillin. In particular examples, two or more of the following antibiotics are used (with each one used on a different detection plate): chloramphenicol, spectinomycin, streptomycin, erythromycin, rifampicin, tetracycline, trimethoprim, optochin, or penicillin.

The array permits for a determination of whether a target bacterium is viable following opsonophagocytosis. In particular examples, the target bacteria are serotype-specific antibiotic-resistant bacteria, such as serotype-specific antibiotic-resistant gram positive bacteria. Gram positive bacteria are known, and in certain examples include *Streptococcus* sp. or *Staphylococcus* sp, such as *Streptococcus pneumoniae, Streptococcus mutans, Streptococcus sobrinus, Streptococcus agalactiae, Streptococcus pyogenes*, and *Staphylococcus aureus*. In some examples, the serotype-specific antibiotic-resistant bacteria include: chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*. In a particular example, the serotype-specific antibiotic-resistant bacteria include or consist of: chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*. One skilled in the art that other serotype-specific antibiotic-resistant bacteria can be used. For example, such bacteria can have a different antibiotic resistance or be resistant to a different growth inhibitor (such as a chemotherapeutic agent). In another example, the bacteria are of a different serotype depending on the pathogen or vaccine of interest. The array can then be customized for the selection of such target bacteria.

The metabolic indicator present in the growth medium 16, 18, 26 can provide a signal indicating viability of bacteria in the absence of counting bacterial colonies on an agar surface. For example, the metabolic indicator can produce a signal in the presence of viable or live bacteria, or in the presence of dead bacteria, depending on the metabolic indicator used. In a particular example, the metabolic indicator produces a fluorescent signal when viable bacteria are present, thereby indicating viability of bacteria. An example of such a metabolic colorimetric indicator is resazurin (also referred to in the art as Alamar Blue™). In another particular example, the metabolic colorimetric indicator produces a fluorescent signal when non-viable or dead bacteria are present. Examples of such metabolic indicators are cell-impermeant nucleic acid stains (which therefore only stain dead cells). The presence of viable bacteria of a particular serotype indicates that the sample tested in the opsonophagocytosis assay does not contain functional antibodies for that serotype. In contrast, absence of viable bacteria of a particular serotype indicates that the sample tested in the opsonophagocytosis assay contains functional antibodies for that serotype.

A specific multi-well, multi-plate example is provided in FIG. 2A. In one example, an array 10 includes at least seven multi-well plates 30, 32, 34, 36, 38, 40, 42, wherein each plate includes a plurality of containers a-l. Although only 12 containers per plate are shown in FIG. 2A, one skilled in the art will appreciate that fewer or greater numbers of containers can be included on each plate, such as 4, 8, 12, 16, 32, 64, 96, 384 or even 1536 containers per plate. For example, FIG. 2B shows a detection panel 42 that has 96 containers. All containers a-l include a growth medium that supports growth of bacteria, and a metabolic indicator. In addition, containers a-l include a growth inhibitory substance. Each plate 30, 32, 34, 36, 38, 40, 42 includes a different growth inhibitory substance in its containers a-l that is associated with a target serotype-specific antibiotic-resistant bacteria for that plate. For example, containers a-l of plate 30 can include chloramphenicol, containers a-l of plate 32 can include spectinomycin, containers a-l of plate 34 can include streptomycin, containers a-l of plate 36 can include optochin, containers a-l of plate 38 can include rifampicin, containers a-l of plate 40 can include penicillin, and containers a-l of plate 42 can include trimethoprim. It will also be recognized by those skilled in the art that a single plate containing multiple containers can be used, wherein subsets of the containers include a particular growth inhibitory substance. For example, containers a-d of plate 30 can include optochin, containers e-h of plate 30 can include rifampicin, and containers i-l of plate 30 can include trimethoprim.

An example of the components present in the containers a-l for each plate 30, 32, 34, 36, 38, 40, 42 is shown in Table 1, along with a list of the target serotype-specific antibiotic-resistant bacteria for that plate. In one example, the concentration of antibiotic in containers a-l is ½ the MIC. In a specific example, the concentration of antibiotic in containers a-l is as follows: containers 30 a-l 4 µg/ml chloramphenicol, containers 32 a-l 154 µg/ml spectinomycin, containers 34 a-l 400 µg/ml streptomycin, containers 36 a-l 1.2 µg/ml optochin, containers 38 a-l 1.5 µg/ml rifampicin, containers 40 a-l 0.5 µg/ml penicillin, and containers 42 a-l 19 µg/ml trimethoprim, such as containers 30 a-l at least 4 µg/ml chloramphenicol, containers 32 a-l at least 154 µg/ml spectinomycin, containers 34 a-l at least 400 µg/ml streptomycin, containers 36 a-l at least 1.2 µg/ml optochin, containers 38 a-l at least 1.5 µg/ml rifampicin, containers 40 a-l at least 0.5 µg/ml penicillin, and containers 42 a-l at least 19 µg/ml trimethoprim.

TABLE 1

Container components and corresponding target bacteria.

| Plate | Growth Medium | Growth inhibitory substance associated with plate | Metabolic indicator | Gram positive target S. pneumoniae strain |
|---|---|---|---|---|
| 30 | Todd-Hewitt Yeast extract broth | chloramphenicol | Alamar Blue ™ | See Bogaert et al.* |
| 32 | Todd-Hewitt Yeast extract broth | spectinomycin | Alamar Blue ™ | 1344387 |
| 34 | Todd-Hewitt Yeast extract broth | streptomycin | Alamar Blue ™ | 1081748 |
| 36 | Todd-Hewitt Yeast extract broth | optochin | Alamar Blue ™ | DS2214-94 |
| 38 | Todd-Hewitt Yeast extract broth | rifampicin | Alamar Blue ™ | 1026409 |
| 40 | Todd-Hewitt Yeast extract broth | penicillin | Alamar Blue ™ | DS1235-99 |
| 42 | Todd-Hewitt Yeast extract broth | trimethoprim | Alamar Blue ™ | 1212458 |

*(Vaccine 22: 4014-20, 2004)

The target bacteria associated with each plate 30, 32, 34, 36, 38, 40, 42 are resistant to and grow in the growth inhibitory substance associated with that plate, but are not resistant to and do not grow in the presence of other growth inhibitory substances associated with the other plates. As shown in FIG. 2, bacteria associated plate 30 are resistant to and grow in the growth medium containing the growth inhibitory substance associated with that plate 30, but are not resistant to and do not grow in the growth medium containing the growth inhibitory substance associated with other plates 32, 34, 36, 38, 40, 42. Similarly, bacteria associated plate 32 are resistant to and grow in the growth medium containing the growth inhibitory substance associated with that plate 32, but are not resistant to and do not grow in the growth medium containing the growth inhibitory substance associated with other plates 30, 34, 36, 38, 40, 42; bacteria associated plate 34 are resistant to and grow in the growth medium containing the growth inhibitory substance associated with that plate 34, but are not resistant to and do not grow in the growth medium containing the growth inhibitory substance associated with other plates 30, 32, 36, 38, 40, 42; bacteria associated plate 36 are resistant to and grow in the growth medium containing the growth inhibitory substance associated with that plate 36, but are not resistant to and do not grow in the growth medium containing the growth inhibitory substance associated with other plates 30, 32, 34, 38, 40, 42; bacteria associated plate 38 are resistant to and grow in the growth medium containing the growth inhibitory substance associated with that plate 38, but are not resistant to and do not grow in the growth medium containing the growth inhibitory substance associated with other plates 30, 32, 34, 36, 40, 42; bacteria associated plate 40 are resistant to and grow in the growth medium containing the growth inhibitory substance associated with that plate 40, but are not resistant to and do not grow in the growth medium containing the growth inhibitory substance associated with other plates 30, 32, 34, 36, 38, 42; and bacteria associated plate 42 are resistant to and grow in the growth medium containing the growth inhibitory substance associated with that plate 42, but are not resistant to and do not grow in the growth medium containing the growth inhibitory substance associated with other plates 30, 32, 34, 36, 38, 40.

The assay system shown in FIG. 2 can be used, for example by selecting a mammalian subject, such as a human, who is vaccinated with a multivalent vaccine. Booster vaccinations can be administered if desired. Following vaccination, for example at least 1 week, at least 1 month, at least 6 weeks, or at least 6 months following the vaccination, a determination of the immune response to the vaccine is made. A biological sample is obtained from the subject, to determine if functional antibodies to the multivalent vaccine are present in the sample, by determining whether the subject's antibodies are capable of inducing opsonophagocytosis of a target antigen, such as one present on a serotype-specific antibiotic-resistant bacterium. For example, a blood sample can be obtained, and serum isolated from the blood. The serum is analyzed using an opsonophagocytosis assay as follows. Serum is incubated in a growth medium that supports viability of mammalian cells, wherein the growth medium includes complement, effector cells (such as HL-60 cells), and a plurality of serotype-specific antibiotic-resistant bacteria. The serotype of the bacteria corresponds to the antigens present in the vaccine administered to the subject. If a functional antibody was produced to one of the serotype-specific antigens in the multivalent vaccine, the antibody will bind to its corresponding serotype-specific antibiotic-resistant bacteria in the presence of complement, and the bacteria will be ingested and killed by the effector cells. If functional antibodies were not produced to one of the serotypes in the multivalent vaccine, the serotype-specific antibiotic-resistant bacteria corresponding to the missing antibody will survive because they will not be ingested by the effector cells. The effector cells are substantially isolated, for example by centrifugation, and the resulting supernatant analyzed for the presence or absence of viable bacteria.

In a particular example, the opsonophagocytosis assay is performed in a multi-well plate, such as a 96-well plate. The plate can include particular wells that include control reactions, such as those containing only one of the plurality of serotype-specific antibiotic-resistant bacteria. After centrifuging the plate under conditions that pellet a substantial number of the effector cells, but not the bacteria, a fraction of the resulting supernatant is introduced into the containers of the array of the present disclosure, such as that shown in FIG. 2A. The array will include containers with growth medium containing a metabolic indicator and a growth inhibitory substance, wherein the growth inhibitory substance corresponds to the target serotype-specific antibiotic-resistant bacteria. The supernatant is incubated with the growth medium for a time sufficient to produce a detectable reaction from the metabolic indicator, wherein the detectable reaction indicates whether viable or non-viable bacteria are present.

For example, if seven different serotype-specific antibiotic-resistant bacteria are used, wherein each set of bacteria is resistant to a particular antibiotic, the resulting supernatant would be introduced into seven different containers, such as containers 30, 32, 34, 36, 38, 40, 42 of FIG. 2A, each containing a different antibiotic. Referring to FIG. 2A, if the opsonophagocytosis assay were performed in a 12-well dish, and seven different serotype-specific antibiotic-resistant bacteria were present in the plurality of serotype-specific antibiotic-resistant bacteria, a fraction of the supernatant from each of the 12 containers (wells) would be introduced into the corresponding containers a-l of plates 30, 32, 34, 36, 38, 40, and 42. For example, if the seven different serotype-specific antibiotic-resistant bacteria were chloramphenicol-resistant serotype 4 *S. pneumoniae*, spectinomycin-resistant serotype 6B *S. pneumoniae*, streptomycin-resistant serotype 9V *S. pneumoniae*, optochin-resistant serotype 14 *S. pneumoniae*, rifampicin-resistant serotype 18C *S. pneumoniae*, penicillin-resistant serotype 19F *S. pneumoniae*, and trimethoprim-resistant serotype 23F *S. pneumoniae*, containers a-l of plate 30 include chloramphenicol, containers a-l of plate 32 include spectinomycin, containers a-l of plate 34 include streptomycin, containers a-l of plate 36 include optochin, containers a-l of plate 38 include rifampicin, containers a-l of plate 40 include penicillin, and containers a-l of plate 42 include trimethoprim.

Methods of Detecting Functional Antibodies

Methods are provided for detecting the presence or absence of serotype-specific antibiotic-resistant bacteria as an indication of the presence or absence of functional antibodies, for example the presence or absence of a plurality of different functional antibodies against multiple bacterial serotypes. The presence of viable serotype-specific antibiotic-resistant bacteria following opsonophagocytosis in the presence of a sample from the subject indicates that the sample does not contain functional antibodies for that serotype, and the absence of viable serotype-specific antibiotic-resistant bacteria following opsonophagocytosis in the presence of a sample from the subject indicates that the sample contains functional antibodies for that serotype. Such methods can be used to determine the effectiveness of multivalent vaccines, such as those for gram-positive bacteria, such as *Streptococcus pneumoniae*.

The inventors have observed agreement between the disclosed multivalent opsonophagocytic assay, and previous opsonophagocytic assays (such as the reference opsonophagocytic assay that requires colony counting) was high for each of seven serotypes included in the vaccine. At least 75% of the titers were within 3 dilutions. Agreement was lower for serotypes 6B, 14, and 18C (75%, 79%, and 83%, respectively were within 3 dilutions). Agreement was ≧92% for all other serotypes. Titers from the disclosed multivalent opsonophagocytic assay were also compared to pre-established median titers from a multi-laboratory study. Agreement was high, ≧83% of the disclosed multivalent opsonophagocytic assay titers were within 3 dilutions of the published median titers for each serotype.

In one example, the method includes incubating effector cells, complement, a plurality of different serotype-specific antibiotic-resistant bacteria, and a biological sample in the presence of a medium that supports viability or growth of the effector cells, wherein the complement and effector cells are present in a sufficient amount to permit opsonophagocytosis and lysis of the bacteria by the effector cells in the presence of functional antibodies to the bacteria. The bacteria are introduced into a liquid growth medium that includes a first growth inhibitory substance and a metabolic indicator that indicates bacterial viability. The medium supports the growth of a first of the plurality of different serotype-specific antibiotic-resistant bacteria, but not the other members of the plurality of bacteria. For example, the growth medium can include a first growth inhibitory substance to which the first of the plurality of different serotype-specific antibiotic-resistant bacteria is resistant to, but to which the other members of the plurality bacteria are not resistant to. The method further includes detecting a change (such as a colorimetric change) of the metabolic indicator that indicates whether the first bacteria is viable, wherein an absence of viability is an indication that the test serum contains functional antibodies that promote complement-mediated opsonophagocytic activity against the first bacteria, and wherein the presence of viability is an indication that the test serum does not contain functional antibodies that promote complement-mediated opsonophagocytic activity against the first bacteria. In particular examples, bacterial colonies are not counted to detect bacterial viability.

In some examples, the plurality of different serotype-specific antibiotic-resistant bacteria are gram positive bacteria that can be opsonophagocytosed in the presence of the complement, the effector cells, and functional antibodies effective against the first of the plurality of different serotype-specific antibiotic-resistant bacteria.

The method can include detecting a plurality of different functional antibodies against multiple bacterial serotypes, for example by using multiple growth media, wherein each medium includes a growth inhibitory substance to which one of the serotype-specific antibiotic-resistant bacteria is resistant but to which the other serotype-specific antibiotic-resistant bacteria are not resistant. For example, the method can further include introducing the plurality of different serotype-specific antibiotic-resistant bacteria into a second growth medium, wherein the second growth medium contains a second growth inhibitory substance and a metabolic colorimetric indicator that indicates bacterial viability of a second of the plurality of different serotype-specific antibiotic-resistant bacteria, wherein the second bacteria is resistant to and grows in the second growth inhibitory substance but not the first inhibitory substance, and the first bacteria is not resistant to the second growth inhibitory substance. Detecting a colorimetric change of the metabolic indicator indicates whether the second of the plurality of different serotype-specific antibiotic-resistant bacteria are viable, wherein an absence of viability is an indication that the test serum contains functional antibodies that promote complement-mediated opsonophagocytic activity against the second bacteria and the presence of viability is an indication that the test serum does not contain functional antibodies against the second of at least one of the plurality of different serotype-specific antibiotic-resistant bacteria.

In a particular example, the plurality of different serotype-specific antibiotic-resistant bacteria are introduced into at least five additional growth media (for a total of seven growth media), wherein each of the at least five additional growth media contain a different growth inhibitory substance and a metabolic indicator that indicates bacterial viability of the plurality of different serotype-specific antibiotic-resistant bacteria, wherein the plurality of different serotype-specific antibiotic-resistant bacteria includes bacteria that are resistant to and grow in one of the growth inhibitory substances in the at least five additional growth media, but not the other growth media containing a different growth inhibitory substance, and the first and the second of the plurality of different serotype-specific antibiotic-resistant bacteria are not resistant to the growth inhibitory substances in the at least five growth media. Detecting a change of the metabolic indicator (such as a colorimetric change) that indicates whether the bacteria that are resistant to and grow in one of the at least five additional growth media are viable, wherein an absence of viability is an indication that the test serum contains functional antibodies against the bacteria that are resistant to and grow in one of the growth inhibitory substances.

In another example, the plurality of different serotype-specific antibiotic-resistant bacteria are introduced into at least two growth media, such as at least three, at least four, at least five, at least six, at least seven, at least eight, at least nine, or even at least 10 growth media. The growth media all include a metabolic indicator that indicates bacterial viability of the serotype-specific antibiotic-resistant bacteria. The growth media also include a growth inhibitory substance, wherein each medium contains a different growth inhibitory substance. In particular examples, each growth inhibitory substance inhibits the growth of all but one of the plurality of different serotype-specific antibiotic-resistant bacteria. Therefore, each of the plurality of different serotype-specific antibiotic-resistant bacteria are resistant to and can grow in the growth medium containing the growth inhibitory substance to which it is resistant. Detecting a colorimetric change of the indicator that indicates whether the bacteria that are resistant to and grow in the growth media are viable, wherein an absence of viability is an indication that the test serum contains functional antibodies against the bacteria that are resistant to and grow in the growth inhibitory substance.

Methods for detecting a plurality of different functional antibodies against multiple bacterial serotypes are disclosed. In particular examples, the method includes combining a biological sample with a plurality of different serotype-specific antibiotic-resistant bacteria, complement, and effector cells, thereby generating a test sample (or reaction mixture). The test sample can also include growth medium that permits viability and metabolic activity of the cells. Ideally, this growth medium does not significantly interfere with the viability of the bacteria. The test sample is incubated for a time sufficient to permit killing of the bacteria by the effector cells (opsonophagocytosis), thereby generating a second reaction mixture. This second reaction mixture, such as a portion thereof, is incubated with a plurality of growth media, wherein each growth medium can support the growth of at least one of the serotype-specific antibiotic-resistant bacteria. For example, the second test sample (or a portion thereof) can be introduced into the disclosed arrays to determine the viability of the bacteria. The growth medium includes a metabolic indicator that indicates bacterial viability and a growth inhibitory substance, wherein the at least one of the serotype-specific antibiotic-resistant bacteria is resistant to and grows in the growth inhibitory substance, but does not grow and is not resistant to the growth inhibitory substances in the other growth media. A signal from the metabolic indicator is detected, wherein the signal indicates opsonophagocytic killing of the bacteria and the presence of functional antibodies in the sample against a particular bacterial serotype, or indicates no opsonophagocytic killing of the bacteria and the absence of functional antibodies to a particular bacterial serotypes (depending on the metabolic indicator used). In some examples, the signal is compared to a control (such as a reference value, for example a signal present when bacteria or viable or not).

In particular examples, the bacteria are incubated in the growth medium (containing a metabolic indicator and a growth inhibitory substance) for a time sufficient to produce a detectable colorimetric reaction in the presence of viable or non-viable bacteria, depending on the metabolic indicator used. For example, if the Alamar Blue™ metabolic indicator is used, the bacteria can be incubated in the growth medium for an amount of time that would produce a colorimetric reaction in the presence of viable bacteria. Such an amount of time can be determined, for example, by growing serotype-specific antibiotic-resistant bacteria in growth medium containing a growth inhibitory substance to which the bacteria are resistant and can grow in, and determining how long it takes to produce a detectable colorimetric reaction. In another example, if a metabolic indicator is used that produces a colorimetric reaction in the presence of dead cells (such as a cell-impermeant nucleic acid stain), the bacteria can be incubated in the growth medium for an amount of time that would produce a colorimetric reaction in the presence of non-viable bacteria. Such an amount of time can be determined, for example, by growing serotype-specific antibiotic-resistant bacteria in growth medium containing a growth inhibitory substance to which the bacteria are not resistant, and determining how long it takes to produce a detectable colorimetric reaction. In particular examples, the amount of time is at least 2 hours, at least 4 hours, such as at least 5 hours, or at least 6 hours. In other examples, the amount of time is less than 24 hours, such as less than 12 hours, less than 8 hours, or less than 6 hours, such as 1-12 hours, 1-8 hours, 2-6 hours, 4-8 hours, or even 4-6 hours.

In some examples, combining the biological sample with a plurality of different serotype-specific antibiotic-resistant bacteria, complement, and effector cells, thereby generating a test sample (or reaction mixture), includes combining the biological sample with the plurality of different serotype-specific antibiotic-resistant bacteria, thereby generating a biological sample-bacteria mixture, incubating the biological sample-bacteria mixture for a time sufficient to permit pre-opsonization; and then adding complement and effector cells to the biological sample-bacteria mixture.

The second reaction mixture can include a portion thereof, such as one that is substantially free of effector cells. In another example, the portion thereof includes viable serotype-specific antibiotic-resistant bacteria that were not opsonophagocytosed by the effector cells. However, if the sample contains functional antibodies for each of the plurality of serotype-specific antibiotic-resistant bacteria, the second reaction mixture may contain no detectable viable bacteria.

The disclosed method can be used to determine if functional antibodies are present in a sample, such as a biological sample obtained from a subject. The sample to be analyzed can be any biological sample obtained from a mammalian subject, such as a human subject. In particular examples, the sample is obtained from a body fluid or tissue of a subject, such as a saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, or nasal secretions. In a specific example, the sample is a serum sample. The sample can be diluted, purified, concentrated, filtered, dissolved, suspended or otherwise manipulated prior to analysis.

In particular examples, the subject has been immunized with a plurality of different antigens, wherein the different antigens correspond to the serotype of the serotype-specific antibiotic-resistant bacteria. In such examples, therefore, determining whether functional antibodies are present in the sample provides an indication of the effectiveness of the immunization and whether the vaccine provides protection for the subject. Only if the sample includes functional antibodies, those that can bind the specific antigen on the serotype-specific antibiotic-resistant bacteria and interact with the effector cell and complement, will lead to the uptake of the bacteria by the effector cell, thereby killing the bacteria. If no viable serotype-specific antibiotic-resistant bacteria of a particular serotype are detected (such as serotype 4) using the disclosed method, this indicates that the sample includes functional antibodies (such as antibodies that are specific for serotype 4), and that the subject from whom the sample was obtained has sufficient protection for that serotype. For example, an OPA titer of at least 8 or more is correlated with protection based on vaccine efficacy trials of pneumococcal conjugate vaccines (Jodar et al., *Vaccine* 21:3065-72, 2003). In contrast, if viable serotype-specific antibiotic-resistant bacteria of a particular serotype are detected (such as serotype 18C) using the disclosed method, this indicates that the sample does not include functional antibodies (such as antibodies that are specific for serotype 18C). Therefore, the subject from whom the sample was obtained does not have sufficient protection for that serotype despite vaccination or exposure to the pathogen.

For example, following administration of a vaccine to a subject and an immune response is generated in the subject a sample suspected of containing functional antibodies can be obtained from the subject and analyzed using the methods disclosed herein. In particular examples, the method includes comparing the relative amount of detected functional antibodies to amounts of functional antibody in the absence of the vaccine, and the effectiveness of the vaccine determined based upon an increase in the amount of functional antibody detected after immunization. In particular examples, functional antibody (or OPA) titers are expressed as the reciprocal of the highest serum dilution yielding at least 50% killing of the bacteria. In particular examples, such as examples where Alamar Blue™ is used as a metabolic indicator, the OPA titer is determined as the reciprocal of the serum dilution at which 50% or lower fluorescent signal is detected as compared to complement control wells (a signal of 20,000 fluorescent units or more). The disclosed methods can also be used to determine whether functional antibodies are generated in response to infection by a particular pathogen.

In some examples, the subject has been immunized with a multivalent vaccine, such as a multivalent vaccine specific for serotypes of one or more gram-positive bacterium. In particular examples, the gram-positive bacterium is *Streptococcus pneumoniae, Streptococcus agalacteae, Streptococcus pyogenes, Staphylococcus aureus, Bacillus* sp., *Clostridium* sp., *Propionibacterium* sp., or *Corynebacterium diphtheria*, among others. However, the disclosed methods are not limited to particular pathogenic organisms. For example, the methods can be used to determine if a subject has functional antibodies to yeast (such as *Candida* sp., *Cryptococcus* sp., and *Blastomyces* sp.), as well as *Mycobacteria* sp. or *Nocardia* sp.

For example, there are multiple serotypes of *S. pneumoniae*. Particular examples of *S. pneumoniae* serotypes include, but are not limited to: 1, 3, 4, 5, 6B, 7F, 8, 9N, 9V, 10A, 11A, 12F, 14, 15B, 17F, 18C, 19A, 19F, 20, 22F, 23F, and 33F. *S. pneumoniae* is the leading cause of meningitis, septicemia, pneumonia and acute otitis media in young children and an important cause of illness and death in the elderly and persons with certain underlying conditions. Host protection against invasive pneumococcal disease is primarily mediated by anti-capsular antibodies and complement-mediated phagocytosis. Since functional opsonophagocytic activity appears to correlate with protection against pneumococcal diseases, the disclosed assays can be used to determine the effectiveness of pneumococcal vaccines.

Serotype-specific antibiotic-resistant bacteria are known in the art. In addition, if not readily available, such bacteria can be generated using methods known in the art. For example, a particular serotype-specific bacteria can be incubated in growth medium containing an appropriate concentration of antibiotic or other growth inhibitory substance of choice, and selecting bacterial clones that can grow in the growth inhibitory substance. Alternatively, an antibiotic resistance marker can be transfected into a wild type strain of a particular serotype. Such methods will allow one to isolate and expand the serotype-specific antibiotic-resistant bacteria of choice.

The growth medium that includes the metabolic indicator and the growth inhibitory substance can further include other substances that permit growth of the particular bacteria used. For example, if the serotype-specific antibiotic-resistant bacteria are Streptococcus pneumoniae, the growth medium that includes the colorimetric metabolic indicator and the growth inhibitory substance can further include Todd-Hewitt Yeast extract broth. In another example, the serotype-specific antibiotic-resistant bacteria are Staphylococcus aureus or Streptococcus pyogenes, and the growth medium that includes the colorimetric metabolic indicator and the growth inhibitory substance further includes Brain Heart Infusion broth.

Examples of serotype-specific antibiotic-resistant bacteria, include, but are not limited to: chloramphenicol-resistant serotype 4 S. pneumoniae, spectinomycin-resistant serotype 6B S. pneumoniae, streptomycin-resistant serotype 9V S. pneumoniae, erythromycin-resistant serotype 14 S. pneumoniae, optochin-resistant serotype 14 S. pneumoniae, rifampicin-resistant serotype 18C S. pneumoniae, tetracycline-resistant serotype 19F S. pneumoniae, penicillin-resistant serotype 19F S. pneumoniae, and trimethoprim-resistant serotype 23F S. pneumoniae.

Growth inhibitory substances can include an agent or combination of agents that reduce or prevent the growth of otherwise viable cells, such as bacterial cells. A particular non-limiting example is an antibiotic, such as chloramphenicol, spectinomycin, streptomycin, erythromycin, optochin, rifampicin, tetracycline, penicillin, trimethoprim, or combinations thereof. In a particular example, the growth inhibitory substances include antibiotics to which the different serotype-specific antibiotic-resistant bacteria are resistant.

Effector cells are cells that can bind to antibody/antigen complexes (such as serum opsonin/polysaccharide complexes) and internalizing such complexes. For example, upon binding of a serotype-specific functional antibody to its corresponding capsular polysaccharide on a serotype-specific bacterium, the effector cell in the presence of complement will internalize and lyse the bacterium, thereby killing the bacterium. Effector cells are in some examples obtained from the serum of an individual or from an in vitro culture. Exemplary effector cells include macrophages, mononuclear phagocytes, natural killer cells, or granulocytes. In one particular example, the effector cells are human promyelocytic leukemia cells, such as the HL-60 cell line. Methods of preparing HL-60 cells are known in the art.

Complement traditionally refers to the heat labile factor in serum that causes immune cytolysis (lysis of antibody coated cells, such as a serotype-specific antibiotic-resistant bacteria cell bound to its corresponding serotype-specific antibody), and can include the entire functionally related system that includes at least 20 serum proteins that are the effector of immune cytolysis and other biologic functions. In particular examples, complement is provided in the form of serum, such as baby rabbit serum. In some examples, complement is freeze-dried prior to use.

Metabolic indicators include substances that produce a color change, wherein the color change indicates whether a cell is viable or proliferating, or whether the cell is dead. In particular examples, a metabolic indicator is used to determine whether a bacterium, such as a serotype-specific antibiotic-resistant bacterium, is viable. In one example, a colorimetric metabolic indicator produces a color if viable cells are present. For example, incubation of cells in Alamar Blue™ (resazurin), dodecyl resazurin ($C_{12}$-resazurin), fluorescein diacetate (FDA) or 5-cyano-2,3-ditolyltetrazolium chloride (CTC) will result in a colorimetric reaction (such as the emission of fluorescence at a particular wavelength of light) upon excitation at a particular wavelength (or range of wavelengths), if viable cells are present. In another example, a colorimetric metabolic indicator produces a color if no-viable or dead cells are present. For example, incubation of cells in a cell-impermeant nucleic acid stain can be used to detect dead or non-viable cells. Excitation of the stain at the appropriate wavelength, such as SYTOX Green nucleic acid stain or SYTOX Blue nucleic acid stain, will emit a particular wavelength of light if dead cells are present.

In particular examples, the signal generated by the metabolic indicator is a change in fluorescence, such as an increase in fluorescence in the presence of viable bacteria, or a decrease in fluorescence in the presence of non-viable bacteria. In some examples, the signal generated by the metabolic indicator is compared to a control (for example a reference value). For example, if the control includes serotype-specific antibiotic-resistant bacteria in growth medium with the metabolic indicator and a growth inhibitor to which the serotype-specific antibiotic-resistant bacteria is resistant, then a decrease in signal relative to the control indicates the absence of viable serotype-specific antibiotic-resistant bacteria, and an increase or similar signal relative to the control indicates the presence of viable serotype-specific antibiotic-resistant bacteria. Similarly, if the control includes serotype-specific antibiotic-resistant bacteria in growth medium with the metabolic indicator and a growth inhibitor to which the serotype-specific antibiotic-resistant bacteria is not resistant, then an increase in signal relative to the control indicates the presence of viable serotype-specific antibiotic-resistant bacteria, and a decrease or similar signal relative to the control indicates the absence of viable serotype-specific antibiotic-resistant bacteria.

In other examples, the signal generated by the metabolic indicator is an increase in fluorescence in the presence of non-viable bacteria, or a decrease in fluorescence in the presence of viable bacteria. In particular examples, the change in fluorescence is relative to a complement control in the absence of antibodies. For example, if the control includes serotype-specific antibiotic-resistant bacteria in growth medium with the metabolic indicator and a growth inhibitor to which the serotype-specific antibiotic-resistant bacteria is resistant, then an increase in signal relative to the control indicates the absence of viable serotype-specific antibiotic-resistant bacteria, and a decrease or similar signal relative to the control indicates the presence of viable serotype-specific antibiotic-resistant bacteria. Similarly, if the control includes serotype-specific antibiotic-resistant bacteria in growth medium with the metabolic indicator and a growth inhibitor to which the serotype-specific antibiotic-resistant bacteria is not resistant, then a decrease in signal relative to the control indicates the presence of viable serotype-specific antibiotic-resistant bacteria, and an increase or similar signal relative to the control indicates the absence of viable serotype-specific antibiotic-resistant bacteria.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Example 1

Preparation of Master Plates and Opsonophagocytosis

This example provides methods for making master plates for opsonophagocytosis assays. Opsonophagocytosis occurs in the master plate, and the resulting mixture (which may contain live bacteria) are then replica plated into one or more plates (or panels) for analysis (see Example 2). Although this provides a particular example that can be used to screen for the presence of 1-7 different S. pneumoniae serotypes, one skilled in the art will appreciate that similar methods can be used for other S. pneumoniae serotypes, as well as for other gram-positive bacteria (or other pathogen) of a particular serotype that are antibiotic resistant.

A similar quality control sera preparation to gammaglobulin (Bayer Co.) was described previously (Romero-Steiner et al., Clin. Diagn. Lab. Immunol. 4:415-422, 1997). A set of twelve paired reference sera (pre/post) from human adult volunteers receiving the 23-valent S. pneumoniae polysaccharide vaccine collected at the Oxford Blood Transfusion Service, Oxford, United Kingdom. Sera were lyophilized and stored at −20° C., re-suspended and stored at −70° C. prior to use. Serum was diluted 2-fold in 10 µl of opsonophagocytosis buffer (Hanks balanced salt solution with 0.1% gelatin) if serum was abundant or 4-fold in 30 µl of opsonophagocytosis buffer if serum was limiting.

The 2-fold dilutions were performed as follows. Undiluted serum (20 µl) was added to a 96 well round-bottom microtiter plate (Costar, Corning, N.Y.) and diluted two fold in-plate into 10 µl opsonophagocytosis buffer (Hanks balanced salt solution with 0.1% gelatin). This yields eight 2-fold dilutions of test serum ranging from 1:8 (row A) to 1:1024 (row H). The 4-fold dilutions were performed as follows. Undiluted serum (10 µl) was added to a 96 well round-bottom microtiter plate (Costar, Corning, N.Y.) and diluted two fold in-plate into 30 µl opsonophagocytosis buffer. This yields eight 4-fold dilutions of test serum with a range of 1:4 (row A) to 1:16,384 (row H).

For example, as shown in Table 2, eight different unknown sera can be added to wells A1-A8 and serially diluted into wells B1-H1, B2-H2, B3-H3, B4-H4, B5-H5, B6-H6, B7-H7, and B8-H8, respectively as desired. For example, for a two fold serum dilution, 20 µl of serum is added to well A1, then serially diluted into wells B1-H1, each containing 10 µl of opsonophagocytosis buffer (the last 10 µl is discarded).

TABLE 2

96 Well Template for 7-valent fmOPA.

| | 1 | 2 | 3 | 4 | 5 | 6 | 7 | 8 | 9 | 10 | 11 12 |
|---|---|---|---|---|---|---|---|---|---|---|---|
| A | Unk1 1:8 | Unk2 | Unk3 | Unk4 | Unk5 | Unk6 | Unk7 | Unk8 | QC1 1:32 | QC2 1:32 | C' type 4 |
| B | 1:16 | | | | | | | | 1:64 | 1:64 | C' type 6B |
| C | 1:32 | | | | | | | | 1:128 | 1:128 | C' type 9V |
| D | 1:64 | | | | | | | | 1:256 | 1:256 | C' type 14 |
| E | 1:128 | | | | | | | | 1:512 | 1:512 | C' type 18C |
| F | 1:256 | | | | | | | | 1:1024 | 1:1024 | C' type 19F |
| G | 1:512 | | | | | | | | 1:2048 | 1:2048 | C' type 23F |
| H | 1:1024 | | | | | | | | | | complement controls. |

All of the wells of Table 2 include opsonophagocytosis buffer, except wells A1 to A10. As a positive control, purified IgG (Bayer, Elkhart, Ind.) was included in the plate (at a dilution of 1:4) in wells A9 and A10, and then serially diluted into rows B9-G9 and B10-G10, respectively, as shown in Table 2.

Serotype-specific S. pneumoniae (Table 3) were added to the wells as follows. For the reference opsonophagocytic assay and the fluorescent oponophagocytic assay (fOPA), seven different S. pneumoniae strains (Table 3) were diluted in opsonophagocytosis buffer (OPA) buffer and added at 1,000 cfu in 20 µl per well. Not all of the S. pneumoniae strains used for the reference and fOPA assay have resistance to a particular antibiotic.

For the multivalent assay (fmOPA), seven different S. pneumoniae strains were used, each strain having a different antibiotic resistance (Table 3). Bacteria were grown to mid log arithmetic phase in Todd Hewitt Yeast Extract media containing the appropriate antibiotic for selection of resistant bacteria. The bacteria were then stored in glycerol at −70° C. When needed, the bacteria were allowed to thaw at room temperature. Each serotype was diluted in OPA buffer, and all seven types mixed to yield a final suspension containing approximately 10,000 cfu per each type (for a total of 70,000 cfu) in a 20 µl volume. Lower numbers of bacteria did not affect the titer (1,000 to 10,000); however the incubation period was extended up to 8 hours to generate sufficient fluorescent signal. The bacterial mixture (20 µl per well) was added to wells containing sera (columns 1-10 of Table 2) and to the complement control wells (H9-H12; 20 µl of complement). Each individual serotype was further diluted 1:10 in opsonophagocytosis buffer for the inoculation of antibiotic growth controls. To this end, fourteen wells (A11-G12) were reserved for adding 20 µl of each diluted serotype individually, in duplicate (Table 2).

TABLE 3

S. pneumoniae strains.

| Serotype | Reference and fOPA Strain | Multivalent fOPA Strain Strain | Antibiotic Resistance | Final Antibiotic Concentration |
|---|---|---|---|---|
| 4 | DS2382-94 | Bogaert et al.* | chloramphenicol | 4 µg/ml |
| 6B | DS2212-94 | Bogaert et al. 1344387* | spectinomycin | 154 µg/ml |
| 9V | DS400-92 | Bogaert et al. 1081748* | Streptomycin | 400 µg/ml |
| 14 | DS2214-94 | DS2214-94# | optochin | 1.2 µg/ml |
| 18C | GP116 | Bogaert et al. 1026409* | rifampicin | 1.5 µg/ml |
| 19F | DS2217-94 | DS1235-99 | penicillin | 0.5 µg/ml |
| 23F | DS2216-94 | Bogaert et al. 1212458* | trimethoprim | 19 µg/ml |

*(Vaccine 22: 4014-20, 2004); #Moon Nahm, University of Alabama at Birmingham

Serum and the bacteria were incubated for 15 minutes at 37° C. and 5% $CO_2$ for pre-opsonization. Subsequently, rabbit complement (Table 1) (10 µl for OPA, fOPA; 20 µl per well for fmOPA) and differentiated and washed HL-60 cells (40 µl containing $4 \times 10^5$ cells per well for OPA and fOPA; 30 µl containing $8 \times 10^5$ cells per well for fmOPA) were added to each well of the plate to bring the final well volume to 80 µl.

Complement was derived from newborn rabbit serum (Pel-Freez, Brown Deer, Wis.) and was kept frozen at −70° C. in 1 ml aliquots until ready to use.

HL-60 cells were maintained in RPMI 1640 media supplemented with 20% fetal bovine serum (Hyclone, Logan, Utah) and antibiotic (penicillin-streptomycin solution, Invitrogen Corp.). Cells were induced to differentiate into polymorphonuclear leukocyte (PMN)-like cells with 100 mM N,N-dimethyl formamide (Fischer-Scientific, Fairlawn, N.J.), and incubated at 37° C., 5% $CO_2$ for five days. The cells were washed twice in opsono wash buffer (Hanks buffer without $Ca^{++}$ and $Mg^{++}$ with 0.2% bovine serum albumin). After the two washes the cells were resuspended in 3 mls of opsonophagocytosis buffer (Hanks buffer with $Ca^{2+}$ and $Mg^{2+}$ [Invitrogen Corp.] and 0.1% gelatin) for use in the assay.

The reaction mixture was incubated for 45 minutes at 37° C. and 5% $CO_2$ with horizontal shaking 200 rpm to permit opsonophagocytosis by HL-60 cells of bacteria having a serotype that matches an antibody present in the serum sample. Subsequently, HL-60 cells were pelleted as follows. For the fmOPA assay, 140 µl opsonophagocytosis buffer was added to each well to bring it to a sufficient volume (220 µl) for replica plating of up to seven plates. No additional buffer was added for the OPA and fOPA plates. The plates were centrifuged at 1000 rpm for 5 minutes (600 g; enough to form an HL-60 cell pellet, while leaving the bacteria in suspension).

Example 2

Preparation of Arrays and Analysis of Antibody Titer

This example describes plates containing a metabolic indicator and growth inhibitory substance, used to determine the antibody titer for each of the seven S. pneumoniae serotypes. Although this example particularly describes the use of Alamar Blue™ as the metabolic indicator, one skilled in the art will appreciate that other metabolic indicators can be used. In addition, although antibiotics are described as the growth inhibitory substance, one skilled in the art will understand that other growth inhibitory substances can be used. In addition, one skilled in the art can determine the appropriate antibiotic concentration for any antibiotic-resistant bacterium used.

Plates were prepared as follows. Alamar Blue™ buffer (40 µl) (25% Todd-Hewift Yeast extract (THYE) broth; 60% opsonophagocytosis buffer (Hanks balanced salt solution with calcium and magnesium supplemented with 0.1% sterile gelatin), 10% Alamar Blue™ [Trek Diagnostic Systems, Cleveland, Ohio], and antibiotic [see Table 3]) was distributed into a plate (96-well). THYE broth was used because it is known to be optimal for growth of pneumococci. However, one skilled in the art will be able to select the appropriate broth for other gram-positive bacterium of interest. A concentration of 10% Alamar Blue™ can be used without causing toxicity to the bacteria or increasing non-specific signal.

For each strain of antibiotic-resistant serotype-specific bacteria, a different plate was prepared, for a total of seven plates (or panels). Each plate contains one antibiotic, as shown in Table 4 (yielding ½ the MIC for each strain). Final concentrations are shown in Table 4:

TABLE 4

Antibiotic concentrations in Alamar Blue ™ arrays.

| Serotype | Antibiotic | Final [antibiotic] in containter |
|---|---|---|
| 4 | Chloramphenicol | 4 µg/ml |
| 6B | Spectinomycin | 154 µg/ml |
| 9V | Streptomycin | 400 µg/ml |
| 14 | Optochin | 1.2 µg/ml |
| 18C | Rifampicin | 1.5 µg/ml |
| 19F | Penicillin | 0.5 µg/ml |
| 23F | Trimethoprim | 19 µg/ml |

Ideally, the plates containing Alamar Blue™ are kept away from the light. If desired, plates can be frozen at −70° C. for at least one month prior to use without affecting the time for signal development or the OPA titers. Therefore, there is one plate or panel for each serotype, with each plate containing the appropriate antibiotic.

Aliquots from the centrifuged master plate containing the fmOPA reaction (Example 1), were replica plated into the plates as follows. Using a robotic liquid handler (Precision 2000), 20 µl of each well of the centrifuged master plate generated in Example 1 was aliquoted into seven separate plates each containing 40 µl of Alamar Blue™ buffer described above. Similar methods were used for the fOPA reactions, except that the buffer in the plate did not contain antibiotic.

The plates were incubated to permit development of the Alamar Blue™ metabolic indicator as follows. Plates were incubated at 37° C., 5% $CO_2$ for 5 to 6 hours or until the metabolic activity of the bacteria changed the Alamar Blue™ to a lavender color and the complement control wells read $\geq$20,000 FU in a fluorometer at 530/590 excitation/emission (BioTek, model FL600, Gain: 75, Winooski, Vt.). Starting at 5 hours of incubation, Serotypes 14, 9V, 23F, 19F, 18C and 4 develop in ascending order. Serotype 6 took 6 to 6.5 hours to develop the desired signal.

Figure 3:
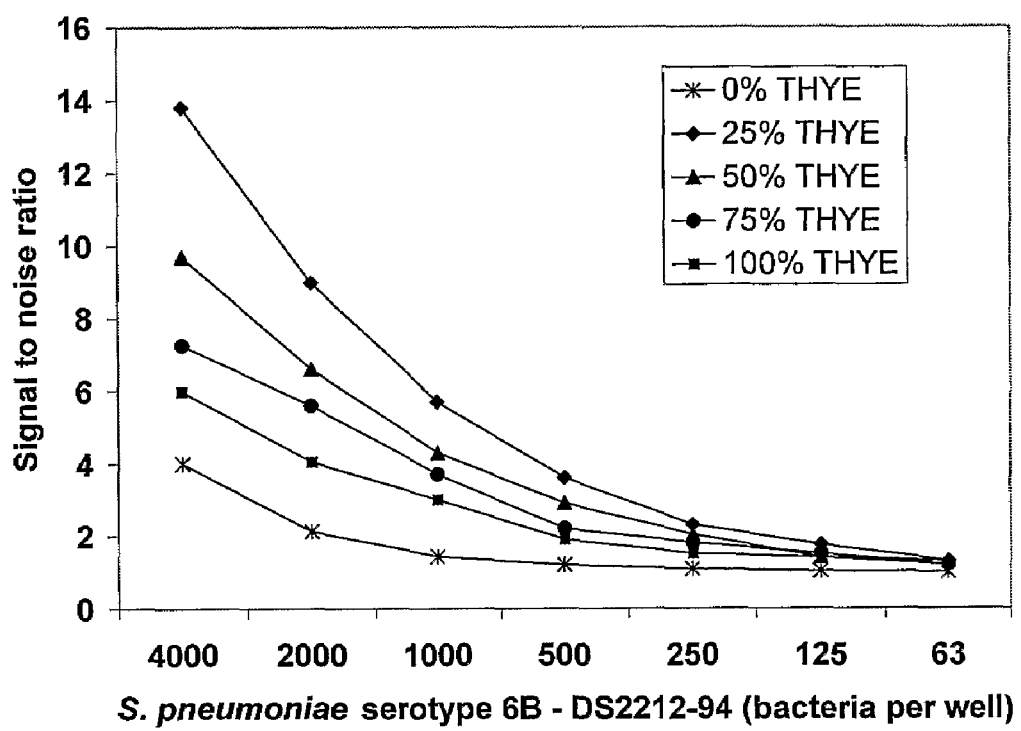
FIG. 3 is a graph showing the signal-to-noise ratios for five Alamar Blue™ reaction mixtures with various bacterial inocula.
Figure 4F:
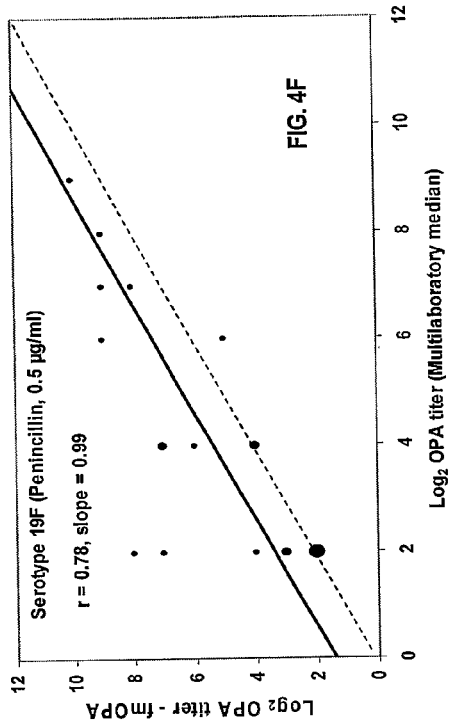
Figure 4E:
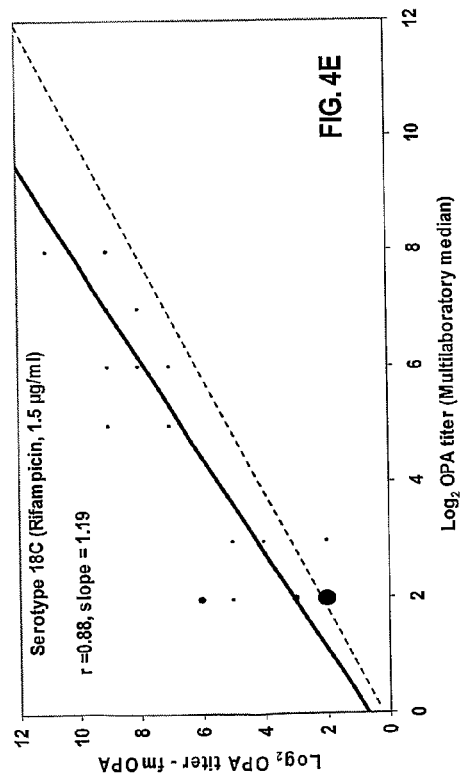
Figure 4G:
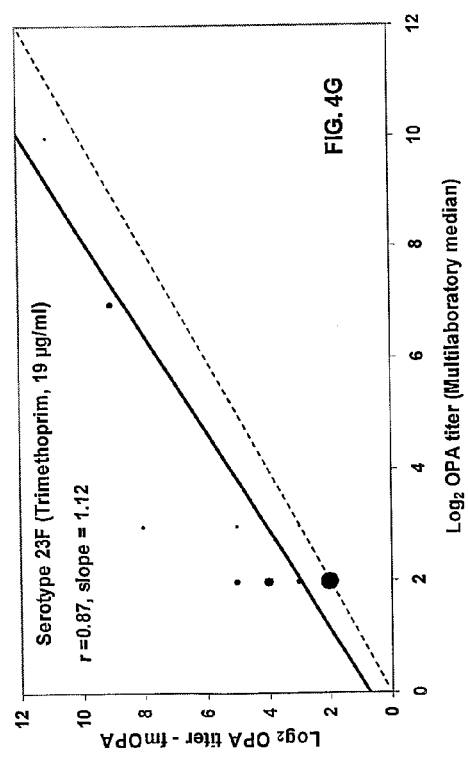

FIG. 3 shows the signal-to noise rations obtained with five different reaction mixtures containing various THYE concentrations and a constant Alamar Blue™ concentration (10%) at various inocula of bacteria. A 10% concentration of Alamar Blue™ in the reaction mixture yielded a final concentration of 6.5% to measure metabolic activity by the bacterial inoculum. Signal was defined as mean fluorescence in the presence of bacteria. Noise was defined as the mean fluorescence of the reagent blanks in the absence of bacteria for each corresponding buffer condition. The total incubation period was four The fluorescent oponophagocytic assay (fOPA) for a single serotype was performed as described in Examples 1 and 2. To evaluate the fluorescent OPA, titers from the single serotype fluorescent assay (fOPA) were compared to titers from the reference OPA with the same target strains, and with colony counting.

Out of the 24 sera (12 pairs) over the seven serotypes, 11-19 (45.8-79.2%, varying by serotype) matched exactly, 1-4 (4.2-16.7%) were within one dilution, 1-8 (4.2-33.3%) were within two dilutions, and 0-4 (0-16.7%) matched within three dilutions (Table 4). For four serotypes (9V, 14, 18C, and 19F), the reference OPA titer and fOPA titer were four or more dilutions apart in 1 sera (4.2%). No sera fell into this category for the other three serotypes. Table 5 shows the cumulative percentages of OPA titers within 1, 2, and 3 dilutions for each serotype. Agreement was good, with the majority of titers matching within 1 dilution, and almost all within three dilutions. Titers were quite comparable to the results obtained for the multilaboratory assay.

TABLE 5

Cumulative percent agreement in titer among OPA methods.

| Serotype | Reference vs. fOPA | | | Reference vs. fmOPA | | | Multilab vs. fmOPA | | |
|---|---|---|---|---|---|---|---|---|---|
| | % $\leq$ 1 | % $\leq$ 2 | % $\leq$ 3 | % $\leq$ 1 | % $\leq$ 2 | % $\leq$ 3 | % $\leq$ 1 | % $\leq$ 2 | % $\leq$ 3 |
| 4 | 70.8 | 83.3 | 100 | 66.6 | 87.5 | 95.8 | 91.7 | 100 | 100 |
| 6B | 79.2 | 95.8 | 100 | 58.3 | 66.6 | 75 | 75 | 95.8 | 100 |
| 9V | 70.8 | 83.3 | 95.8 | 58.3 | 70.8 | 91.7 | 75 | 83.3 | 91.7 |
| 14 | 66.7 | 87.5 | 95.8 | 41.2 | 66.6 | 79.2 | 45.8 | 66.7 | 83.3 |
| 18C | 50 | 79.2 | 95.8 | 62.5 | 79.2 | 83.3 | 58.3 | 75 | 87.5 |
| 19F | 54.2 | 87.5 | 95.8 | 62.5 | 83.3 | 91.7 | 62.5 | 75 | 91.7 |
| 23F | 95.8 | 100 | 100 | 79.2 | 91.6 | 100 | 62.5 | 87.5 | 95.8 | hours. Reaction mixtures contained various concentrations of THYE and a constant concentration of Alamar Blue™. The mixtures were tested with several concentrations of *S. pneumoniae* serotype 6B, reference strain DS2212-94 (63 to 4,000 CFU in a 20 μl well volume). At 4,000 CFU, the signal ranged from 82,358 FU with 25% THYE to 93,714 FU for 100% THYE. The blanks ranged from 5,966 FU with 25% THYE to 15,660 FU with 100% THYE. The greatest signal-to-noise ration was obtained with 25% THYE.

Example 3

Comparison of Opsonophagocytic Assay Using Alamar Blue™ to Standard Viability Method with Colony Counting This example describes methods used to compare single serotype assays using Alamar Blue™ to indicate viability of bacteria, to the standard viability method with colony counting. Identical sera were also analyzed using the standard reference method and a single serotype fluorescent method. Titers from each of these assays were compared.

The reference opsonophagocytic assay (OPA) used was conducted as previously reported (Romero-Steiner et al., *Clin. Diag. Lab. Immunol.* 4:415-22, 1997). The opsonophagocytosis portion of the this assay is described in Example 1, except effector cells differentiated for five days were used at an effector to target cell ratio of 400:1. Following the opsonophagocytosis, the reaction was plated onto a solid medium containing agar and the resulting colonies counted.

Example 4

Fluorescent Multivalent Opsonophagocytic Assay (fmOPA) for *S. pneumoniae*

This example describes methods used for a particular multivalent opsonophagocytic assay to screen for the presence of seven different *S. pneumoniae* serotypes. One skilled in the art will appreciate that similar methods can be used for other *S. pneumoniae* serotypes, as well as for other gram-positive bacteria of a particular serotype that are antibiotic resistant.

The fmOPA was performed in a multivalent format, using a mixture containing all seven serotypes, each with a different antibiotic resistance marker for serotype selection (see Examples 1 and 2). Titers from this assay were compared to the viability data described above and to pre-established median titers from a multi-laboratory study where five separate laboratories assayed the same sera using a single serotype viability assay. Titers that were 3 dilutions away from the median OPA titer were repeated, and the median values of all repeats used for further analysis. Cumulative percent of titers that were within 1, 2, and 3 or more dilutions was calculated. Linear regression analysis of the $Log_2$ transformed OPA titers were used for determining r values and slopes.

The fmOPA titers were compared to values from the in house reference OPA used in the fluorescent OPA validation. Among the seven serotypes, 8-13 sera (33.3-54.2%) matched exactly in titer, 1-6 sera (4.2-25%) were within one dilution, 2-6 (8.3-25%) were within two dilutions, 1-5 (4.2-20.8%) were within three dilutions, and 0-6 (type 6B) sera gave titers four or more dilutions apart. Cumulative percentages within 1, 2 and 3 dilutions are displayed in Table 5. Serotypes 4, 9V, 19F, and 23F all had very high agreement, 92% or more matched within three dilutions. Agreement was lower for serotypes 6B, 14, and 18C, with 75%, 79.2%, and 83.3%, respectively within three dilutions.

The fmOPA titers were also compared to published median values from a multilaboratory study where five different laboratories ran the same 24 sera using the reference OPA method but different strains of bacteria (Romero-Steiner et al., *Clin. Diag. Lab. Immunol.* 11:89-93, 2004). By this comparison, 7-16 sera (29.2-66.6%) matched titer exactly, 2-7 sera (8.3-29.2%) gave titers one dilution apart, 2-6 (8.3-25%) were two dilutions apart, 0-4 (0-16.7%) were three dilutions apart, and 0-4 sera (0-16.7%) gave titers 4 or more dilutions apart. Cumulative percentages are shown in Table 4.

The data were plotted in identity graphs for regression analysis. The $Log_2$ of the titers were plotted, making each of the comparisons described above. FIGS. 4A-G are examples of plots of fmOPA titers against the median values from the multilaboratory study for seven serotypes with high, medium, and low agreement. Comparison of titers from the reference OPA method with those from the fOPA, yielded r values ranging from 0.98 to 0.79, and slopes between 1.0 and 0.71. In comparison of the same standard reference method titers to the fmOPA, the r values ranged from 0.66 to 0.92, and the slopes from 0.37 to 0.78. Finally, in comparing the fmOPA titers to median values from the multilaboratory study gave r values ranging from 0.76 to 0.97 and slopes from 1.19 to 0.47. These data are presented in Table 6.

Agreement was high, ≧83% of fmOPA titers were within 3 dilutions of the published median titers for each serotype. When compared to the viability data from the Alamar Blue™ validation, ≧75% of the titers were within 3 dilutions. Agreement was lower for serotypes 6B, 14, and 18C (≧75%, ≧79%, and ≧83%, respectively were ≦3 dilutions). Agreement was ≧90% for all other serotypes.

TABLE 6

Linear regression analysis (r value and slope) among OPA methods.

| Serotype | Reference v. fOPA | | Reference v. fmOPA | | Multilab v. fmOPA | |
| --- | --- | --- | --- | --- | --- | --- |
| | r | Slope | r | Slope | r | Slope |
| 4 | 0.89 | 0.97 | 0.87 | 0.77 | 0.97 | 1.03 |
| 6B | 0.94 | 0.88 | 0.71 | 0.37 | 0.85 | 0.71 |
| 9V | 0.84 | 0.92 | 0.66 | 0.41 | 0.76 | 0.47 |
| 14 | 0.92 | 1.0 | 0.85 | 0.57 | 0.84 | 0.55 |
| 18C | 0.79 | 0.71 | 0.75 | 0.71 | 0.88 | 1.19 |
| 19F | 0.91 | 0.93 | 0.76 | 0.69 | 0.78 | 0.99 |
| 23F | 0.98 | 1.0 | 0.92 | 0.78 | 0.87 | 1.12 |

In summary, in particular examples, the disclosed opsonophagocytic assay uses less serum, combines seven serotypes in one assay, and can be completed in a single day while producing comparable titers to those obtained using previous opsonophagocytic assays. High levels of agreement were observed between the fluorescent method and the fluorescent multivalent method to the reference OPA method. The sera that produced the most variable results tended to be those that had high titers for many of the serotypes. Almost all of the sera that were negative by the standard OPA were also negative by the fmOPA. The arrays disclosed in this application allow for the detection of highly reproducible titers that correlate to those measured by the reference OPA viability assay without the need for counting of colony forming units.

Example 5

Selection of Serotype-Specific Antibiotic-Resistant Gram Positive Bacteria

This example describes methods used to identify a strain of *S. pneumoniae* serotype 19F bacteria that is resistant to penicillin (see Example 2). Similar methods can be used to identify gram positive bacteria that are resistant to any antibiotic of interest, such as *S. pneumoniae* serotype 6B bacteria that are resistant to erythromycin.

An overview of the method is as follows. The Active Bacterial Core Surveillance database was searched for recent isolates (identified in the field by the latex method [see below] and by a ≧10 mm zone of inhibition around Optochin disks when grown in blood agar plates) of the given serotype predetermined by the Quellung test; see below). The Minimal Inhibitory Concentrations (MIC) to the antibiotic was then determined. A subgroup of potential strains that can be used for OPA assays were selected. The phenotype (opaque or transparent) for all the strains selected was determined. Strains (2-5) that were of the correct antimicrobial pattern and the opaque phenotype were expanded. Each strain was tested for its antimicrobial selection and growth curves in the metabolic indicator, such as the plates described in Example 2. The antibiotic concentration was optimized as needed to make the panel selective for that serotype, and not cross-reactive for the other serotypes (low background signal). Once the target strain is selected, quality control sera (such as 5-10) are tested for reproducibility of opsonophagocytic titers. If the OPA titers are not in agreement with the reference viability OPA, then that strain is no longer used, and a new strain is tested.

The latex agglutination test for *S. pneumoniae* was performed as follows. From overnight growth in TSA 5% SBA, one half of a 10 µl loop of cells was transferred to 200-300 µl of PBS (pH 7.2). On a clean glass slide latex reagent (serum, glycine buffer, and 2% Latex suspension) was mixed with cell suspension in a 1:1 ratio. A visible 4+ clumping of the suspension is a positive result.

Quellung typing of *S. pneumoniae* was performed as follows. A cell suspension from the latex test was diluted with sterile water. Antiserum (4-5 µl) and methylene blue (1:1) were mixed on a clean glass slide and 0.2 µl of the diluted cell suspension was added and mixed. This smear was covered with a cover slip and incubated at room temperature for 10-15 min. The slide was examined under oil immersion lens. Appearance of capsule as sharply demarcated halo around the dark blue stained cells is a positive reaction.

The antibiotic resistance profile of *S. pneumoniae* isolates was determined as follows. *S. pneumoniae* isolates were examined for their antibiotic resistance profile for 17 antibacterial compounds (erythromycin, penicillin, amoxicillin, cefotaxime, sparfloxacin, ciprofloxacin, tetracycline, clindamycin, chloramphenicol, trimethoprim-sulphamethaxazole, vancomycin, meropenem, levofloxacin, cefuroxime, linezid, synercid, and rifampin) on the basis of minimal inhibitory concentration (MIC). Custom made antibacterial MIC panels (PML Microbiologicals, Wilsonville, Oreg.) were used. Panels were stored frozen (−70° C.) until use. Pneumococcus cultures were grown overnight in blood agar and resuspended in Mueller-Hinton broth (Remel, Lenexa, Kans.) to a turbidity of 0.5 McFarland standard ($1.5 \times 10^8$ CFU/ml). One ml of this bacterial suspension was diluted with 29 ml of sterile water. MIC panels were thawed to room temperature, the test bacterium was inoculated (50 µl/well) with a 96 well titer plate inoculator, and incubated at 37° C., 5% $CO_2$ for 16 to 18 hours. Both single and multiple antibiotic resistances were determined according to NCCLS standards.

Example 6

Effect of Freezing Panels Containing Alamar Blue™ and Antibiotic

This example describes methods used to demonstrate that plates containing Alamar Blue™ and antibiotic in liquid medium (Example 2) can be frozen without significant loss of performance.

Panels (96-well plates) containing Alamar Blue™ and antibiotic in liquid medium were generated as described in Example 2. Plates were frozen at −70° C. for 1-3 months. After 1, 2, and 3 months, panels were thawed and used for evaluation of OPA titers as described in Example 2.

It was observed that OPA titers were not affected when the panels were frozen for up to two months. OPA titers were within 2 dilutions of the OPA titers obtained when using freshly prepared panels (not frozen). However, the time to obtain the fluorescent signal in the complement controls increased by 30 minutes with each month of storage following the first month. No increased incubation time was observed at 1 month of storage.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. An array for detecting *Streptococcus pneumoniae* following opsonophagocytosis, wherein the array comprises:
   a plurality of containers comprising wells present on at least seven multi-well plates, wherein the wells on each plate contain a different growth inhibitory substance associated with a target serotype-specific antibiotic-resistant *Streptococcus pneumoniae* for that plate and wherein the target *Streptococcus pneumoniae* associated with each plate are resistant to and grow in the growth inhibitory substance associated with that plate, but are not resistant to and do not grow in the presence of other growth inhibitory substances associated with the other plates and wherein the different growth inhibitory substances comprise 4 μg/ml chloramphenicol, 154 μg/ml spectinomycin, 400 μg/ml streptomycin, 1.5 μg/ml rifampicin, 19 μg/ml trimethoprim, 1.2 μg/ml optochin, and 0.5 μg/ml penicillin,
      a growth medium that supports growth of the target serotype-specific antibiotic-resistant *Streptococcus pneumoniae* associated with that plate, and
      a metabolic colorimetric indicator comprising a fluorescent signal indicating bacterial viability.

2. The away of claim 1, wherein the containers present on each plate are in a spaced apart alignment to define a matrix of at least eight rows and twelve columns.

3. The array of claim 1, wherein the metabolic colorimetric indicator provides a fluorescent signal indicating viability of *Streptococcus pneumoniae* in the absence of counting bacterial colonies on an agar surface.

4. The array of claim 1, wherein the metabolic colorimetric indicator comprises resazurin.

5. The away of claim 1, wherein the containers do not include agar.

6. The array of claim 1, wherein the different growth inhibitory substances consist of 4 μg/ml chloramphenicol, 154 μg/ml spectinomycin, 400 μg/ml streptomycin, 1.5 μg/ml rifampicin, 19 μg/ml trimethoprim, 1.2 μg/ml optochin, and 0.5 μg/ml penicillin.

7. The away of claim 1, wherein the growth inhibitory substance is present at a concentration of at least of a minimum inhibitory concentration (MIC).

8. The array of claim 1, wherein the growth medium comprises:
   25% Todd-Hewitt Yeast extract (THYE) broth; and
   60% opsonophagocytosis buffer.

9. The away of claim 4, wherein the resazurin is at a concentration of 10%.

10. A method of performing a functional assay for determining if antibodies that promote complement mediated opsonophagocytic activity are present in a test sample, the method comprising:
    incubating effector cells, complement, a plurality of different serotype-specific antibiotic resistant *Streptococcus pneumoniae*, and a test sample in the presence of a medium that supports viability of the effector cells, wherein the complement and effector cells are present in a sufficient amount to lyse the *Streptococcus pneumoniae* in the presence of functional antibodies to the *Streptococcus pneumoniae*;
    introducing the *Streptococcus pneumoniae* into the array of claim 1; and
    detecting a fluorometric change of the metabolic colorimetric indicator that indicates whether the *Streptococcus pneumoniae* is viable, wherein an absence of viability is an indicator that the test serum contains functional antibodies that promote complement mediated opsonophagocytic activity against the *Streptococcus pneumoniae*.

11. The method of claim 1, wherein bacterial colonies are not counted to detect bacterial viability.

12. A method of detecting a plurality of serotype-specific antibiotic-resistant *Streptococcus pneumoniae* following osponophagocytosis, comprising:
    combining a biological sample with a plurality of different serotype-specific antibiotic-resistant *Streptococcus pneumoniae*, complement, and effector cells, thereby generating a test sample;
    incubating the test sample to allow lysis of the *Streptococcus pneumoniae* by the effector cells in the presence of complement and functional antibodies that specifically bind the *Streptococcus pneumoniae*, thereby generating a second test sample;
    incubating a portion of the second test sample with the array of claim 1; and
    detecting a fluorescent signal from the metabolic colorimetric indicator, wherein a change in signal indicates opsonophagocytic killing of the *Streptococcus pneumoniae* and the presence of functional antibodies in the sample against multiple *Streptococcus pneumoniae* serotypes.

13. The method of claim 12, wherein combining a biological sample with a plurality of different serotype-specific antibiotic-resistant *Streptococcus pneumoniae*, complement, and effector cells, thereby generating a test sample, comprises:
    combining the biological sample with the plurality of different serotype-specific antibiotic-resistant *Streptococcus pneumoniae*, thereby generating a sample-bacteria mixture;
    incubating the sample-bacteria mixture for a time sufficient to permit pre-opsonization; and adding complement and effector cells to the sample-bacteria mixture.

14. The method of claim 12, wherein the portion of the second test sample is substantially free of effector cells.

15. The method of claim 12, wherein the different serotype-specific antibiotic-resistant *Streptococcus pneumoniae* comprise: chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, or trimethoprim-resistant serotype 23 F *Streptococcus pneumoniae*.

16. The method of claim 12, wherein the biological sample is obtained from a body fluid or tissue of a subject.

17. The method of claim 16, wherein the subject has been immunized with a plurality of different antigens, wherein the different antigens correspond to the serotype of the different serotype-specific antibiotic-resistant *Streptococcus pneumoniae*.

18. The method of claim 12, wherein the change in signal comprises a decrease in fluorescence from the metabolic colorimetric indicator.

\* \* \* \* \*

UNITED STATES PATENT AND TRADEMARK OFFICE
CERTIFICATE OF CORRECTION

PATENT NO. : 7,642,068 B2
APPLICATION NO. : 11/910517
DATED : January 5, 2010
INVENTOR(S) : Steiner et al.

It is certified that error appears in the above-identified patent and that said Letters Patent is hereby corrected as shown below:

In the Claims:

Claim 2, Column 29, line 57, "The away" should read -- The array --

Claim 5, Column 29, line 66, "The away" should read -- The array --

Claim 7, Column 30, line 7, "of at least of a" should read
-- of at least ½ of a --

Claim 9, Column 30, line 13, "The away" should read -- The array --

Signed and Sealed this

Ninth Day of November, 2010

David J. Kappos
*Director of the United States Patent and Trademark Office*